(12) United States Patent
Schaffer et al.

(10) Patent No.: US 9,725,746 B2
(45) Date of Patent: *Aug. 8, 2017

(54) PRODUCING AMINES AND DIAMINES FROM A CARBOXYLIC ACID OR DICARBOXYLIC ACID OR A MONOESTER THEREOF

(71) Applicant: Evonik Degussa GmbH, Essen (DE)

(72) Inventors: Steffen Schaffer, Herten (DE); Jasmin Corthals, Bochum (DE); Mirja Wessel, Bochum (DE); Hans-Georg Hennemann, Bedburg (DE); Harald Haeger, Luedinghausen (DE); Michael Volland, Duelmen (DE); Martin Roos, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 15 days.

This patent is subject to a terminal disclaimer.

(21) Appl. No.: 14/649,414

(22) PCT Filed: Dec. 18, 2013

(86) PCT No.: PCT/EP2013/077069
§ 371 (c)(1),
(2) Date: Jun. 3, 2015

(87) PCT Pub. No.: WO2014/095986
PCT Pub. Date: Jun. 26, 2014

(65) Prior Publication Data
US 2015/0307906 A1    Oct. 29, 2015

(30) Foreign Application Priority Data
Dec. 21, 2012 (EP) ..................... 12199048

(51) Int. Cl.
| | | |
|---|---|---|
| *C12P 13/00* | (2006.01) | |
| *C12N 9/02* | (2006.01) | |
| *C12N 9/06* | (2006.01) | |
| *C12N 9/10* | (2006.01) | |
| *C12N 9/12* | (2006.01) | |
| *C12N 15/52* | (2006.01) | |

(52) U.S. Cl.
CPC .......... *C12P 13/001* (2013.01); *C12N 9/0008* (2013.01); *C12N 9/0016* (2013.01); *C12N 9/0069* (2013.01); *C12N 9/1096* (2013.01); *C12N 9/1288* (2013.01); *C12N 15/52* (2013.01); *C12Y 102/01042* (2013.01); *C12Y 104/01001* (2013.01); *C12Y 113/11* (2013.01); *C12Y 207/08007* (2013.01); *Y02P 20/582* (2015.11)

(58) Field of Classification Search
CPC ..... C12P 13/001; C12P 13/005; C12N 9/1288
USPC ....................................... 435/128
See application file for complete search history.

(56) References Cited

U.S. PATENT DOCUMENTS

| | | | |
|---|---|---|---|
| 6,620,970 B2 | 9/2003 | Schiffer et al. | |
| 6,639,108 B2 | 10/2003 | Schiffer et al. | |
| 6,861,540 B2 | 3/2005 | Herwig et al. | |
| 6,878,836 B2 | 4/2005 | Haas et al. | |
| 7,030,052 B2 | 4/2006 | Stochniol et al. | |
| 7,049,450 B2 | 5/2006 | Hofen et al. | |
| 7,091,384 B2 | 8/2006 | Jaeger et al. | |
| 7,507,862 B2 | 3/2009 | Stochniol et al. | |
| 7,608,738 B2 | 10/2009 | Herwig et al. | |
| 7,879,938 B2 | 2/2011 | Häger et al. | |
| 8,022,201 B2 | 9/2011 | Roos et al. | |
| 8,168,841 B2 | 5/2012 | Herwig et al. | |
| 8,232,333 B2 | 7/2012 | Haeger et al. | |
| 8,372,595 B2 | 2/2013 | Schaffer et al. | |
| 8,378,127 B2 | 2/2013 | Dingerdissen et al. | |
| 8,399,658 B2 | 3/2013 | Hengstermann et al. | |
| 8,445,720 B2 | 5/2013 | Hannen et al. | |
| 8,703,451 B2 | 4/2014 | Haas et al. | |
| 8,703,993 B2 | 4/2014 | Hannen et al. | |
| 8,809,576 B2 | 8/2014 | Schraven et al. | |

(Continued)

FOREIGN PATENT DOCUMENTS

| | | |
|---|---|---|
| WO | 2009 077461 | 6/2009 |
| WO | 2010 042664 A2 | 4/2010 |

(Continued)

OTHER PUBLICATIONS

PCT/EP2013/077069 written opinion ISA (Feb. 22, 2013).*
U.S. Appl. No. 14/380,483, filed Aug. 22, 2014, Schiemann, et al.
U.S. Appl. No. 14/367,610, filed Jun. 20, 2014, Haas, et al.
U.S. Appl. No. 14/435,339, filed Apr. 13, 2015, Engel, et al.
U.S. Appl. No. 14/405,050, filed Dec. 2, 2014, Haas, et al.
Kaulmann, U., et al., "Substrate spectrum of w-transaminase from Chromobacterium violaceum DSM30191 and its potential for biocatalysis", Enzyme and Microbial Technology, XP55026143, vol. 41, No. 5, (2007), pp. 628-637.
Schrewe, M., et al., "Direct Terminal Alkylamino-Functionalization via Multistep Biocatalysis in One Recombinant Whole-Cell Catalyst", Adv. Synth. Catal., XP55116393, vol. 355, No. 9, (2013), pp. 1693-1697.

(Continued)

*Primary Examiner* — Tekchand Saidha
(74) *Attorney, Agent, or Firm* — Oblon, McClelland, Maier & Neustadt, L.L.P.

(57) ABSTRACT

The invention relates to a whole-cell catalyst which expresses a recombinant α-dioxygenase or the combination of a recombinant fatty acid reductase and a phosphopantetheinyl transferase which phosphopantetheinylates the fatty acid reductase, and which expresses, in addition to the α-dioxygenase and/or the combination of fatty acid reductase and phosphopantetheinyl transferase, a transaminase, wherein the phosphopantetheinyl transferase and/or transaminase is preferably recombinant; and also to a process for converting a carboxylic acid or dicarboxylic acid or a monoester thereof to an amine or diamine, comprising the steps of contacting the carboxylic acid or dicarboxylic acid or the monoester thereof with a phosphopantetheinylated fatty acid reductase or an α-dioxygenase and contacting the product with a transaminase.

13 Claims, 1 Drawing Sheet

(56) References Cited

U.S. PATENT DOCUMENTS

| | | |
|---|---|---|
| 8,835,691 B2 | 9/2014 | Klasovsky et al. |
| 8,871,862 B2 | 10/2014 | Pawlik et al. |
| 8,911,982 B2 | 12/2014 | Schaffer et al. |
| 8,927,773 B2 | 1/2015 | Klasovsky et al. |
| 8,946,463 B2 | 2/2015 | Klasovsky et al. |
| 8,980,594 B2 | 3/2015 | Reinecke et al. |
| 8,981,159 B2 | 3/2015 | Klasovsky et al. |
| 8,999,684 B2 | 4/2015 | Poetter et al. |
| 9,000,223 B2 | 4/2015 | Micoine et al. |
| 9,005,928 B2 | 4/2015 | Schaffer et al. |
| 9,012,227 B2 | 4/2015 | Karau et al. |
| 2002/0087036 A1 | 7/2002 | Haas et al. |
| 2007/0281345 A1 | 12/2007 | Binder |
| 2010/0068773 A1 | 3/2010 | Marx et al. |
| 2010/0105955 A1 | 4/2010 | Alibhai et al. |
| 2010/0266518 A1 | 10/2010 | Springer et al. |
| 2010/0291644 A1 | 11/2010 | Marx et al. |
| 2010/0298612 A1 | 11/2010 | Behrouzian et al. |
| 2010/0324257 A1 | 12/2010 | Karau et al. |
| 2011/0118433 A1 | 5/2011 | Pötter et al. |
| 2011/0171702 A1 | 7/2011 | Reinecke et al. |
| 2011/0251399 A1 | 10/2011 | Dingerdissen et al. |
| 2012/0034665 A1 | 2/2012 | Haas et al. |
| 2012/0264877 A1 | 10/2012 | Haeger et al. |
| 2012/0315366 A1 | 12/2012 | Zehnacker et al. |
| 2013/0052700 A1 | 2/2013 | Poetter et al. |
| 2013/0092232 A1 | 4/2013 | Pawlik et al. |
| 2013/0092233 A1 | 4/2013 | Pawlik et al. |
| 2013/0149756 A1 | 6/2013 | Sporleder et al. |
| 2013/0164797 A1 | 6/2013 | Gielen et al. |
| 2013/0165685 A1 | 6/2013 | Hannen et al. |
| 2013/0171388 A1 | 7/2013 | Pawlik et al. |
| 2013/0207050 A1 | 8/2013 | Hermasch et al. |
| 2013/0240799 A1 | 9/2013 | Haeger et al. |
| 2013/0299750 A1 | 11/2013 | Hermasch et al. |
| 2014/0039210 A1 | 2/2014 | Erhardt et al. |
| 2014/0054224 A1 | 2/2014 | Erhardt et al. |
| 2014/0120587 A1 | 5/2014 | Haas et al. |
| 2014/0141478 A1 | 5/2014 | Schaffer et al. |
| 2014/0178948 A1* | 6/2014 | Schaffer ............... C12P 13/001 435/128 |
| 2014/0186905 A1 | 7/2014 | Schaffer et al. |
| 2014/0199736 A1 | 7/2014 | Köhler et al. |
| 2014/0242646 A1 | 8/2014 | Poetter et al. |
| 2014/0256904 A1 | 9/2014 | Schaffer et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |
| 2015/0099282 A1 | 4/2015 | Haas et al. |
| 2015/0111253 A1 | 4/2015 | Schaffer et al. |
| 2015/0111254 A1 | 4/2015 | Hennemann et al. |
| 2015/0209775 A1 | 7/2015 | Erhardt et al. |
| 2015/0218600 A1 | 8/2015 | Haas et al. |

FOREIGN PATENT DOCUMENTS

| | | |
|---|---|---|
| WO | 2010 042664 A3 | 4/2010 |
| WO | 2010 135624 A2 | 11/2010 |
| WO | 2010 135624 A3 | 11/2010 |
| WO | 2007 142784 | 12/2010 |
| WO | 2011 131420 | 10/2011 |
| WO | 2011 154503 | 12/2011 |
| WO | 2012 025629 | 3/2012 |
| WO | 2013 135650 | 9/2013 |
| WO | 2013 149864 | 10/2013 |
| WO | 2015 028423 | 3/2015 |

OTHER PUBLICATIONS

Simon, R.C., et al., "Recent Developments of Cascade Reactions Involving w-Transaminases", ACS Catalysis, XP55116474, vol. 4, No. 1, (2014), pp. 129-143.

European Search Report Issued Feb. 22, 2013 in European Patent Application No. 12199048.5 Filed Dec. 21, 2012.

International Search Report Issued May 20, 2014 in PCT/EP2013/077069 Filed Dec. 18, 2013.

* cited by examiner

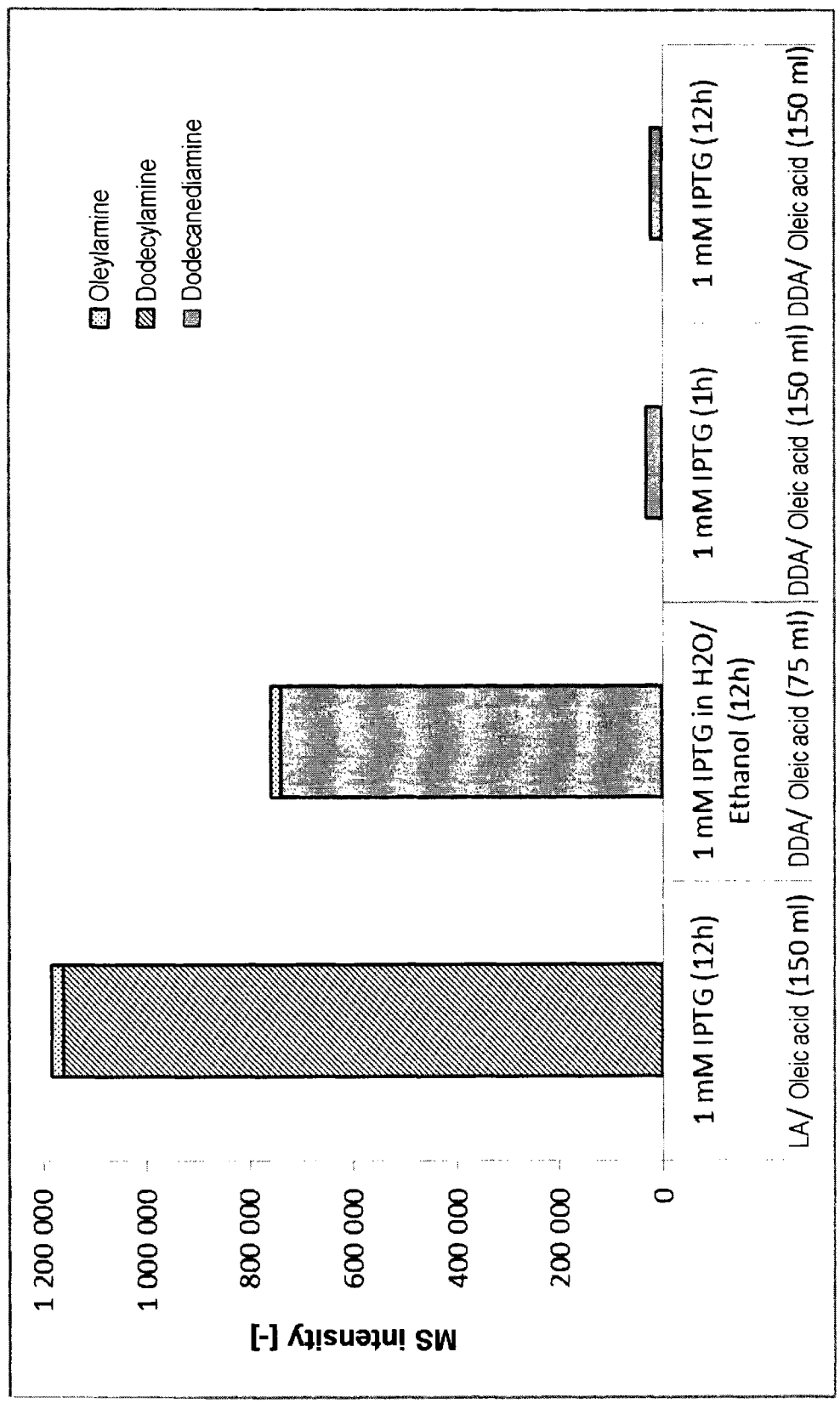

PRODUCING AMINES AND DIAMINES FROM A CARBOXYLIC ACID OR DICARBOXYLIC ACID OR A MONOESTER THEREOF

The invention relates to a whole-cell catalyst which expresses a recombinant α-dioxygenase and/or the combination of a recombinant fatty acid reductase and of a phosphopantetheinyl transferase which phosphopantetheinylates the fatty acid reductase, and which additionally expresses a transaminase, wherein the phosphopantetheinyl transferase and/or transaminase is preferably recombinant; and also to a process for converting a carboxylic acid or dicarboxylic acid or a monoester thereof to an amine or diamine, comprising the steps of contacting the carboxylic acid or dicarboxylic acid or the monoester thereof with a phosphopantetheinylated fatty acid reductase or an α-dioxygenase and contacting the product with a transaminase.

Polyamides are a class of polymers which are characterized by repeating amide groups. In contrast to the chemically related proteins, the term "polyamide" usually relates to synthetic, commercially available, thermoplastic polymers. Polyamides are derived from primary amines or from secondary amines which are conventionally obtained via cracked hydrocarbons. However, it is also possible to use derivatives, more precisely aminocarboxylic acids, lactams and diamines, for producing the polymer. Also of interest as starting materials are short-chain, gaseous alkanes which can be obtained proceeding from renewable raw materials using biotechnological processes.

The conventional chemical-technical production of such amines and diamines is dependent on the supply of fossil raw materials, inefficient, and in the process large amounts of undesired by-products are produced, in some steps of the synthesis up to 80%. An example of such a process is the production of laurolactam. Conventionally, this is carried out via a multi-stage process which not only delivers a low yield, but also simultaneously requires the provision of a complex infrastructure.

In view of the said disadvantages, processes have been developed in order to obtain amines and diamines using biocatalysts starting from renewable raw materials. Suitable renewable raw materials are in particular sources of fatty acids which can be obtained in the form of rapeseed oil, globe thistle oil, palm kernel oil, coconut oil, sunflower kernel oil and similar natural products from a large number of biological sources, in particular from plants.

PCT/EP 2008/067447 describes a biotechnological system for producing chemically related products, more precisely ω-aminocarboxylic acids, using a cell which has a series of suitable enzymatic activities and is able to convert carboxylic acids to corresponding ω-aminocarboxylic acid. The process comprises a cascade of enzymatically catalysed reactions, more particularly the oxidation of a fatty acid at the terminal carbon atom to the aldehyde and the subsequent amination using a transaminase and an amino acid as amine donor, which can be regenerated via an amino acid dehydrogenase.

A known disadvantage of the AlkBGT oxidase system from *Pseudomonas putida* GPO1 used therein, however, is that it is not able to achieve selective oxidation of aliphatic alkanes to primary alcohols. Rather, a multitude of oxidation products arise; in particular, the fraction of more highly oxidized products, such as the corresponding aldehyde, ketone or the corresponding carboxylic acid, increases with increasing reaction time (C. Grant, J. M. Woodley and F. Baganz (2011), *Enzyme and Microbial Technology* 48, 480-486), which correspondingly reduces the yield of desired amine.

The problem of the relatively unselective oxidation is exacerbated by the fact that the corresponding oxidation products are structurally very similar. This means that it is very difficult to separate them off from the desired oxidation products efficiently and without a significant loss in yield.

A further disadvantage of this process is that overoxidized by-products, for example the dicarboxylic acid of the fatty acid used as reactant, the recycling of hydrophobic solvents and hydrophobic liquid cation exchangers which can be used as per PCT/EP2011/071491 for removing the product from the aqueous reaction mixture, are damaging to efficiency in resource utilization.

In this connection, it should be emphasized that the complexity of biotechnological systems having a cascade of reactions such as the one described in PCT/EP 2008/067447, wherein each reaction is catalysed by a particular enzyme, makes it difficult to optimize the reaction conditions. For instance, in the case of the fundamentally reactive ω-amino fatty acids as product, there is the possibility that, from a certain critical concentration inside the cell, they react with essential constituents of the organism and thus have a toxic effect. If this is the case, the growth and synthesis capacity of the organism is impaired through to cell death, without the developer being able to immediately recognize the toxicity or to even assign it to a particular reactant, intermediate product or product. Which organism tolerates which concentration of a chemically reactive substance is likewise not predictable.

Also with regard to a product yield that is to be improved and a by-product development that is to be reduced, a person skilled in the art cannot routinely identify limiting and critical factors in a system such as the one described in PCT/EP2008/067447. If the yield of product is too low, this can be due to the fact that one of the enzymes is present in an excessively low concentration, without it being known which of the possible enzymes it is, i.e. the reactant is not converted within the intended period or before degradation by competing enzymes owing to insufficient synthesis capacity. Alternatively, it is by all means possible that an enzyme is indeed detectable in the cell in the form of a polypeptide, but, specifically in this cell, does not have the folding essential to the activity or lacks a hitherto unknown cofactor that is, however, essential to the activity. Similarly, as already mentioned, the metabolic product may be toxic to the cell or be degraded. Lastly, interfering interactions with endogenous enzymes, i.e. enzymes naturally present in a cell used as whole-cell catalyst, should be expected.

There is therefore a need for processes for producing alkyl monoamines and diamines from fatty acids, in which the enzymatically catalysed reactions proceed more selectively and the formation of undesired by-products is minimized.

Against this background, it is an object of the invention to provide a biotechnological process for producing alkyl monoamines and diamines from fatty acids that is as efficient as possible with regard to yield, carbon and/or nitrogen balance and/or purity.

It is also an object of the invention to provide a biotechnological process for producing alkyl monoamines and diamines from fatty acids that is as efficient as possible with regard to yield, carbon and/or nitrogen balance, reusability of agents used and/or purity of the product. In this connection, an efficient carbon and/or nitrogen balance is preferably understood as meaning that a very high proportion of the carbon and/or nitrogen fed to a cell for converting a carboxylic acid or a carboxylic ester in the form of suitable substrates is recovered in the desired final product, instead of, for example, being converted to products other than the one desired.

It is also an object of the invention to improve the ability of a multi-phase reaction mixture from the production of alkyl monoamines and diamines from fatty acids to be worked up, especially with regard to reusability relating to work-up of used hydrophobic solvent and liquid cation exchanger, and also with regard to phase formation and separation in a biphasic system comprising an aqueous phase in which the conversion of the carboxylic acid or the carboxylic ester proceeds, and an organic phase containing organic solvents and/or liquid cation exchangers.

These and further objects are achieved by the subject matter of the present application and in particular also by the subject matter of the accompanying independent claims, the dependent claims specifying embodiments of the invention.

In a first aspect, the object underlying the invention is achieved by a whole-cell catalyst which expresses a recombinant α-dioxygenase or the combination of a recombinant fatty acid reductase and of a phosphopanteteinyl transferase which phosphopanteteinylates the fatty acid reductase, and which additionally expresses a transaminase, wherein the phosphopanteteinyl transferase and/or transaminase is preferably recombinant.

In a first embodiment of the first aspect, the object is achieved by a whole-cell catalyst which additionally expresses an amino acid dehydrogenase which is preferably recombinant.

In a second embodiment, which is also an embodiment of the first embodiment, the object is achieved by a whole-cell catalyst which additionally expresses an alkane hydroxylase which is preferably recombinant.

In a third embodiment, which is also an embodiment of the first to second embodiment, the object is achieved by a whole-cell catalyst which additionally expresses a polypeptide of the AlkL family, which polypeptide is preferably recombinant.

In a fourth embodiment, which is also an embodiment of the second embodiment, the object is achieved by a whole-cell catalyst which additionally expresses an alcohol dehydrogenase which is preferably recombinant.

In a fifth embodiment, which is also an embodiment of the first to fourth embodiment, the object is achieved by a whole-cell catalyst, wherein the activity of at least one enzyme involved in the β-oxidation is reduced with respect to the wild type of the whole-cell catalyst.

In a sixth embodiment, which is also an embodiment of the first to fifth embodiment, the object is achieved by a whole-cell catalyst, wherein the activity of BioH or a variant thereof is reduced or elevated with respect to the wild type of the whole-cell catalyst.

In a seventh embodiment, which is also an embodiment of the first to sixth embodiment, the object is achieved by a whole-cell catalyst, wherein the activity of FadL or a variant thereof is elevated with respect to the wild type of the whole-cell catalyst.

In a second aspect, the object underlying the invention is achieved by a process for converting a carboxylic acid or dicarboxylic acid or a monoester thereof to an amine or diamine, comprising the steps of
a) providing a carboxylic acid or dicarboxylic acid or a monoester thereof, in the case of a dicarboxylic acid, preferably by contacting a carboxylic acid with an alkane hydroxylase and/or alcohol dehydrogenase,
b) contacting the carboxylic acid or dicarboxylic acid or the monoester thereof with a phosphopanteteinylated fatty acid reductase or an α-dioxygenase to form an aldehyde product, and
c) contacting the product from step a) with a transaminase.

In a second aspect, the object underlying the invention is achieved by a process, wherein an amino acid dehydrogenase is present in step c).

In a first embodiment of the second aspect, the object is achieved by a process, wherein at least one enzyme from the group comprising phosphopanteteinylated fatty acid reductase, α-dioxygenase, transaminase, amino acid dehydrogenase and alkane hydroxylase, preferably all the enzymes used from said group, are provided in the form of a whole-cell catalyst the first aspect of the present invention.

In a second embodiment, which is also an embodiment of the first embodiment, the object is achieved by a process, wherein the carboxylic acid or dicarboxylic acid or the monoester thereof is a compound of the formula (I)

$$R^1\text{-A-COOR}^2 \qquad (I),$$

where $R^1$ is selected from the group comprising —H and $COOR^3$,
where $R^2$ and $R^3$ are each independently selected from the group comprising H, methyl, ethyl and propyl,
with the proviso that at least one of the radicals $R^2$ and $R^3$ is H,
where A is an unbranched, branched, linear, cyclic, substituted or unsubstituted hydrocarbon group having at least four carbon atoms.

In a third embodiment, which is also an embodiment of the first to second embodiment, the object is achieved by a process, wherein A has the formula —$(CH_2)_n$—, where n is at least 4, preferably at least 10.

In a third aspect, the object underlying the invention is achieved by using the whole-cell catalyst according to the first aspect or the process according to the second aspect for aminating a fatty acid, ω-hydroxy fatty acid, ω-oxo fatty acid or a monoester thereof.

In a fourth aspect, the object underlying the invention is achieved by a reaction mixture comprising the whole-cell catalyst according to the first aspect in aqueous solution and also a fatty acid, ω-hydroxy fatty acid, ω-oxo fatty acid or a monoester thereof of the formula (I)

$$R^1\text{-A-COOR}^2 \qquad (I),$$

where $R^1$ is selected from the group comprising —H, —CHO, —OH and $COOR^3$,
where $R^2$ and $R^3$ are each independently selected from the group comprising H, methyl, ethyl and propyl,
with the proviso that at least one of the radicals $R^2$ and $R^3$ is H,
where A is an unbranched, branched, linear, cyclic, substituted or unsubstituted hydrocarbon group having at least four carbon atoms, preferably the formula —$(CH_2)_n$—, where n is at least 4, particularly preferably at least 10.

The present invention is based on the finding by the inventor that a functionally recombinant fatty acid reductase or α-dioxygenase in a whole-cell catalyst which is used to produce amines and diamines from fatty acids and has a corresponding enzyme environment surprisingly increases the yield of amines and diamines.

Furthermore, the present invention is based on the finding by the inventor that a functionally recombinant fatty acid reductase or α-dioxygenase in a whole-cell catalyst which is used to produce amines and diamines from fatty acids and has a corresponding enzyme environment surprisingly reduces the concentration of interfering by-products, more particularly overoxidized fatty acids in the form of dicarboxylic acids and esters thereof, in the product which arises.

Furthermore, the present invention is based on the finding by the inventor that a functionally recombinant fatty acid reductase or α-dioxygenase in a whole-cell catalyst which is used to produce amines and diamines fatty acids and has a corresponding enzyme environment improves the purity and reusability of liquid cation exchangers such as oleic acid, which are used to remove the amine and diamine from a fermentation solution comprising the whole-cell catalyst.

The present invention provides an improved process for converting a carboxylic acid or dicarboxylic acid or a monoester thereof to an amine or diamine, which process is notable for the fact that, besides the enzymes catalyzing the transfer of the fatty acid via its various oxidation stages to the amine, a fatty acid reductase or α-dioxygenase is also present, preferably when a whole-cell catalyst is used to carry out the process. In a preferred embodiment, the term "fatty acid reductase", as used herein, is understood to mean an enzyme which catalyzes the conversion of a ω-carboxylic acid, also referred to as dicarboxylic acid or ω-carboxy fatty acid, to the corresponding ω-oxo fatty acid with consumption of ATP and NAD(P)H. In the prior art, for example in WO/2010/135624, fatty acid reductases for producing ω-hydroxy fatty acids are described, but not as part of a system for producing ω-amino fatty acids. In an even more preferred embodiment, the fatty acid reductase is selected from the group of fatty acid reductases comprising the amino acid sequences YP_887275.1, ZP_11001941.1, ZP_06852401.1, NP_959974.1, YP_001070587.1, ZP_05217435.1, YP_882653.1, YP_639435.1, ZP_10800193.1, YP_006452763.1, YP_006730440.1, ZP_11196216.1, YP_005349252.1, ZP_05224908.1, YP_005338837.1, YP_006307000.1, YP_005343991.1, ZP_11001942.1, ZP_09979565.1, YP_005003162.1, YP_953393.1, YP_001850422.1, ZP_11011489.1, ZP_12689264.1, YP_905678.1, ZP_09976919.1, YP_004746059.1, NP_217106.1, YP_004525443.1, NP_337166.1, ZP_09685823.1, YP_978699.1, ZP_06437984.1, ZP_06514086.1, NP_856267.1, CAA19077.1, NP_301424.1, ZP_06522140.1, ZP_06518098.1, ZP_11008938.1, ZP_07432374.2, AAR91681.1, YP_006808747.1, YP_001851230.1, ZP_15327751.1, ZP_15455857.1, ZP_12874284.1, ZP_15332534.1, ZP_15512956.1, ZP_14244106.1, ZP_15470899.1, ZP_11439367.1, YP_001703694.1, ZP_15446742.1, YP_006808978.1, ZP_07964926.1, YP_006521379.1, ZP_10796908.1, ZP_15512957.1, ZP_12874283.1, YP_005350955.1, ZP_14243341.1, YP_001705436.1, ZP_15329649.1, YP_006522325.1, YP_006732197.1, YP_003658971.1, ZP_05227804.1, YP_001703695.1, YP_006308707.1, ZP_15342047.1, YP_006521380.1, ZP_15327752.1, YP_005340557.1, ZP_11439578.1, ZP_15392943.1, YP_15514789.1, ZP_12996178.1, ZP_09412214.1, ZP_06849686.1, YP_889972.1, YP_006570321.1, ZP_15375693.1, YP_006308219.1, YP_006521600.1, YP_005340029.1, YP_005350457.1, ZP_11439836.1, ZP_12994664.1, ZP_14240588.1, ZP_14236860.1, ZP_09410830.1, YP_006731697.1, YP_005264225.1, YP_001704097.1, ZP_15328186.1, ZP_09402885.1, ZP_12690463.1, AFO59871.1, ZP_07966879.1, YP_118225.1, YP_001828302.1, YP_006566873.1, YP_003660169.1, ZP_15337407.1, ZP_08240521.1, ZP_10456477.1, YP_001537947.1, YP_004016539.1, ZP_07664024.1, ZP_14244107.1, ZP_09794557.1, ZP_09274211.1, ZP_05224899.1, ZP_15484175.1, AAA17105.1, ZP_11437924.1, ZP_15446621.1, YP_003646340.1, ZP_15382134.1, ZP_14237669.1, ZP_09165547.1, YP_004019203.1, ZP_14240225.1, YP_001220863.1, CBA74242.1, ZP_12994240.1, EIE27140.1, ZP_15354547.1, ZP_15432557.1, ZP_15500132.1, ZP_15478632.1, ZP_06846978.1, AAA17108.1, ZP_15333767.1, ZP_05217205.1, AAD44234.1, YP_005348984.1, YP_006306749.1, ZP_05224611.1, YP_005343772.1, YP_006730188.1, YP_882425.1, ZP_10799956.1, ZP_05045132.1, NP_960176.1, ZP_12398880.1, ZP_11192735.1, ZP_11440091.1, ZP_05217203.1, ZP_06846979.1, ZP_10800936.1, ZP_06523596.1, YP_882421.1, YP_006306748.1, YP_006522017.1, ZP_15432556.1, ZP_15354095.1, ZP_05227781.1, ZP_09684639.1, YP_006730187.1, YP_005343770.1, YP_005338616.1, YP_005348983.1, ZP_15472813.1, ZP_15457007.1, ZP_15421152.1, ZP_15488933.1, ZP_14240030.1, YP_001704825.1, ZP_15328982.1, YP_005911512.1, ZP_09411638.1, ZP_12786400.1, ZP_12995435.1, ZP_07667680.1, YP_001281387.1, EIE21044.1, ZP_15375054.1, NP_334518.1, 4DQV_A, ZP_06435375.1, YP_003030020.1, YP_976237.1, ZP_04926822.1, YP_004998149.1, YP_004743589.1, YP_005907921.1, NP_214615.1, YP_001286047.1, ZP_06515541.1, ZP_05139482.1, YP_888016.1, ZP_06452908.1, ZP_06519578.1, YP_004721827.1, CAJ77696.1, ZP_09680854.1, ZP_09686453.1, YP_884815.1, YP_884815.1, CAB55600.1, ZP_09081423.1, YP_006521568.1, ZP_11440626.1, ZP_15513309.1, ZP_09410778.1, ZP_15374248.1, ZP_15405954.1, YP_001704047.1, ZP_14236911.1, ZP_12873916.1, ZP_14242094.1, ZP_12994610.1, ZP_07664023.1, ZP_15446620.1, ZP_15484174.1, ZP_14240245.1, YP_005358845.1 and XP_002669159.1, more particularly YP_006731697.1, ZP_09839660.1, YP_001704097.1, YP_889972.1, ZP_05045132.1, ZP_09794557.1, ZP_08240521.1, NP_959974.1, ZP_10456477.1, YP_118225.1, NP_217106, YP_905678.1, YP_887275.1, ZP_11001941.1, YP_953393.1 and YP_005349252.1 variants thereof.

Fatty acid reductases are a group of enzymes which require for their activity a phosphopantetheinylation, i.e. the covalent attachment of a phosphopantetheinyl cofactor to the enzyme. Accordingly, the fatty acid reductase used according to the invention is phosphopantetheinylated, and a whole-cell catalyst expressing the fatty acid reductase expresses, either as part of its environment of endogenously expressed enzymes or in recombinant form, a phosphopantetheinyl transferase which phosphopantetheinylates the fatty acid reductase. In a preferred embodiment, the term "phosphopantetheinyl transferase", as used herein, is understood to mean an enzyme which transfers a phosphopantetheinyl moiety from a phosphopantetheinyl-CoA to an enzyme, preferably to the fatty acid reductase. In a particularly preferred embodiment, the phosphopantetheinyl transferase is selected from the group of phosphopantetheinyl transferases comprising the amino acid sequences ABI83656.1, YP_006811024.1, YP_120266.1, YP_005265173.1, YP_004006671.1, ZP_08152482.1, ZP_11104141.1, ZP_14482198.1, YP_706581.1, ZP_10002626.1, ZP_09308410.1, YP_002783881.1, ZP_18276502.1, ZP_09271851.1, ZP_08204640.1, YP_002766085.1, ZP_09788717.1, ZP_09799863.1, ZP_10961877.1, YP_003273299.1, GAB86168.1, YP_006668875.1, ZP_08766535.1, ZP_09793386.1, ZP_09212827.1, ZP_09276344.1, ZP_09213870.1, ZP_09081490.1, ZP_10947586.1, YP_003658841.1, ZP_06852853.1, YP_953148.1, ZP_11011170.1, YP_639258.1, YP_886985.1, ZP_11194383.1, ZP_09681094.1, ZP_06455719.1, NP_337369.1, YP_004077819.1, NP_217310.1, YP_006452521.1, YP_005339056.1, ZP_05226335.1, ZP_07965127.1, ZP_07419314.2, NP_302077.1, YP_005003342.1, YP_005349465.1, ZP_10800435.1, ZP_06564430.1, YP_882860.1, YP_001135287.1, YP_001850220.1, ZP_05217634.1, YP_003646683.1, YP_004746246.1, ZP_15327906.1, ZP_09979035.1, YP_001703848.1, YP_906028.1, ZP_15395499.1, ZP_11438833.1, ZP_11005955.1, ZP_09410582.1, NP_961833.1, YP_001106197.1, ZP_14237113.1, YP_004085491.1, YP_003835595.1, ZP_12994399.1, YP_004523804.1, ZP_12690887.1, YP_003339468.1, ZP_06589331.1, YP_004801334.1, ZP_09974565.1, ZP_04608379.1, ZP_13037142.1, YP_712537.1, ZP_11236665.1, NP_630748.1, ZP_06527138.1, YP_003835167.1, CCH33620.1, ZP_10309401.1, ZP_08881396.1, YP_003102953.1, YP_003487252.1, ZP_08881565.1, YP_006263961.1, NP_822924.1, YP_004914569.1, ZP_09400366.1, AFV71333.1, ZP_07309518.1, ZP_09172171.1, ZP_06710898.1, CAN89630.1, ZP_06921116.1, ZP_08804003.1, ZP_19189663.1, ZP_10545589.1, YP_006248725.1, ZP_10455557.1, YP_004015869.1, ZP_08801530.1, ZP_10550999.1, YP_004492879.1, ZP_09958730.1, ZP_08286666.1, ZP_11212856.1, AAL15597.1, AAZ94407.1, ZP_19188802.1, AFF18625.1, ZP_06575404.1, AAK06801.1, ADC79635.1, YP_004080528.1, YP_004921314.1, ACY01405.1, YP_004584022.1, YP_003114157.1, YP_003203177.1, AFB69911.1, YP_006876460.1, ZP_08024798.1, YP_006269867.1, YP_006881814.1, CCK26150.1, ZP_07307765.1, ZP_07315112.1, YP_005466392.1, NP_824081.1, YP_003493882.1, ZP_06412387.1, ZP_10068239.1, ZP_08234258.1, YP_001822177.1, ZP_03979107.1, ZP_07979043.1, BAA22407.1, ZP_09402950.1, YP_003112617.1, NP_738483.1, YP_480609.1, EKX90208.1, BAE93744.1, BAB69186.1, ZP_04713061.1, YP_006881735.1, ZP_07274901.1, ZP_11379052.1, ZP_06581115.1, YP_006437406.1, ZP_12871839.1, NP_601186.1, ZP_08451808.1, YP_005057339.1, YP_005303909.1, ZP_07090824.1, YP_003783676.1, YP_004630011.1, ZP_06588772.1, AAX98203.1, AFK80329.1, ZP_08124665.1, ZP_03710365.1, AAB17877.1, ZP_07403633.1, ZP_11268660.1, ZP_07288841.1, ABV83217.1, ZP_16178576.1, AAG43513.1, ZP_09155938.1, YP_004605750.1, ZP_03918977.1, AAF71762.1, ZP_05007864.1, ZP_06836265.1, ZP_03934882.1, YP_001508477.1, ZP_06043756.1, ZP_05366306.1, YP_002835056.1, ZP_03933464.1, ZP_07469321.1, ZP_07713507.1, YP_005160553.1, NP_939820.1, AAU93794.1, ZP_14659796.1, ZP_14383679.1, YP_005058606.1, YP_001221073.1, ZP_08231568.1, YP_250920.1, ZP_11383249.1, YP_003916320.1, ZP_08681170.1, YP_001800249.1, YP_001157632.1, YP_166099.1, ZP_10088015.1, YP_004760065.1, ZP_07947675.1, YP_001603066.1, YP_003812683.1, YP_004403402.1, ZP_08292153.1, ZP_09471260.1, YP_004018108.1, ZP_05115352.1, AAD13565.1, ZP_09295321.1, YP_001535629.1, ZP_04607273.1, YP_006561753.1, ZP_00960958.1, YP_006571985.1, ZP_08862188.1, YP_002906426.1, CCK30433.1, ZP_13042493.1, ZP_09090153.1, YP_614397.1, ZP_11163860.1, YP_003983492.1, YP_004080668.1, ZP_09420475.1, ZP_05914565.1, ZP_01101149.1, ZP_14743088.1, YP_001239694.1, ZP_09127532.1, YP_003833873.1, ZP_08516197.1, ZP_10160483.1, ZP_01987188.1, ZP_01755304.1, ZP_08825027.1, ZP_05077116.1, YP_001444606.1, ZP_03392800.1, ZP_01057781.1, AFB69889.1, ZP_08815097.1 and AAO17175.1 and variants thereof. In a particularly preferred embodiment, the phosphopantetheinyl transferase is the one having the database code ABI83656.1 or a variant thereof.

As an alternative or in addition to the combination of fatty acid reductase and phosphopantetheinyl transferase, the whole-cell catalyst can also comprise an α-dioxygenase. In a preferred embodiment, the term "α-dioxygenase", as used herein, is understood to mean an enzyme which catalyzes the conversion of a carboxylic acid and/or dicarboxylic acid or a monoester thereof with consumption of a molecule of oxygen and with elimination of a carbon dioxide molecule to a carboxylic acid and/or dicarboxylic acid or a monoester thereof which bears an aldehyde group at the terminal ω-carbon atom and is shortened by one carbon atom at the terminal ω-carbon atom with respect to the carboxylic acid and/or dicarboxylic acid or a monoester thereof used as reactant. In a particularly preferred embodiment, the α-dioxygenase is selected from the group of α-dioxygenases comprising the amino acid sequences NP_001066718.1, EAY82977.1, BAH79993.1, ABG22011.1, BAJ90503.1, AFD04418.1, AFD04417.1, BAJ87736.1, AFW75180.1, ABG22012.1, XP_002311389.1, CAH05011.1, XP_002279884.1, CBI34957.3, AAG59584.1, NP_001234414.1, NP_001234410.1, XP_003553942.1, XP_002275161.1, XP_003553937.1, CBI34960.3, CAA07589.1, XP_003543402.1, XP_002517402.1, XP_002882184.1, NP_186791.1, AAK85133.1, CAN77070.1, XP_002529555.1, CAH64542.1, NP_001234061.1, XP_002281357.1, ADM21465.1, XP_002318527.1, NP_177509.1, CAN74266.1, XP_002888940.1, NP_001185393.1, XP_003631072.1, BAJ33800.1, XP_002517377.1, XP_003530944.1, BAJ34623.1, ABG22013.1, ABP02610.1, XP_001773135.1, XP_002960339.1, ABK95279.1, ABD73303.1, ABD73304.1, YP_001805721.1, ZP_08971815.1, ZP_08430366.1, YP_823013.1, ZP_05026427.1, ZP_11003953.1, YP_007064484.1, YP_007113008.1, YP_633369.1, ZP_18906570.1, ZP_09251410.1, ZP_10050808.1, ZP_01306662.1, YP_001516886.1, ZP_05042862.1, AAC49625.1, ZP_09648375.1, ZP_09792714.1, ZP_09788527.1, XP_001728273.1, AAC83355.1, YP_890542.1, ZP_11000891.1, XP_002605323.1, EGO58341.1, YP_006249145.1, YP_001507004.1, YP_001704637.1, ZP_12876141.1, ZP_11150830.1, ZP_14236257.1, ZP_09411385.1, ZP_14243118.1, EKD16664.1, ZP_15416799.1, ZP_15338016.1, ZP_10080295.1, ZP_11438929.1, ZP_12995210.1, ZP_10946648.1, YP_003409541.1, XP_001637870.1, YP_005451221.1, XP_001212758.1, ZP_07290489.1, ZP_05781329.1, ZP_19187748.1, ZP_06574534.1, XP_002605322.1, NP_822950.1, YP_006366425.1, EJP63377.1, EKD21217.1, XP_001795927.1, XP_003042615.1, ZP_06566152.1, EGU88116.1, EFY94417.1, XP_388327.1, EKJ68934.1, ZP_07290463.1, CCC10458.1, YP_001107201.1, XP_003348248.1, T49753, CAD31840.1, XP_001229975.1, CBN77040.1, YP_004813753.1, XP_002513273.1, XP_001627136.1, AFG52858.1, AFG52857.1, AEW08450.1, NP_841291.1, YP_004512343.1, ACG75701.1 and ZP_03500906.1 and variants thereof. In a particularly preferred embodiment, the α-dioxygenase is the one having the database code NP_001066718.1 or a variant thereof.

Besides the α-dioxygenase or the combination of fatty acid reductase and the phosphopantetheinyl transferase, the whole-cell catalyst according to the invention needs to have a transaminase which aminates terminal aldehyde groups. In a preferred embodiment, the term "transaminase", as used herein, is understood to mean an enzyme which catalyzes the transfer of α-amino groups from a donor molecule, preferably an amino acid, to an acceptor molecule, preferably an α-ketocarboxylic acid. In a particularly preferred embodiment, the transaminase is selected from the group of transaminases comprising the amino acid sequences 3HMU_A, AAD41041.1, AAK15486.1, ABE03917.1, ADR60699.1, ADR61066.1, ADR62525.1, AEL07495.1, CAZ86955.1, EFW82310.1, EFW87681.1, EGC99983.1, EGD03176.1, EGE58369.1, EGH06681.1, EGH08331.1, EGH24301.1, EGH32343.1, EGH46412.1, EGH55033.1, EGH62152.1, EGH67339.1, EGH70821.1, EGH71404.1, EGH78772.1, EGH85312.1, EGH97105.1, EGP57596.1, NP_102850.1, NP_106560.1, NP_248912.1, NP_248990.1, NP_354026.2, NP_421926.1, NP_637699.1, NP_642792.1, NP_744329.1, NP_744732.1, NP_747283.1, NP_795039.1, NP_901695.1, XP_002943905.1, YP_001021095.1, YP_001059677.1, YP_001061726.1, YP_001066961.1, YP_001074671.1, YP_001120907.1, YP_001140117.1, YP_001170616.1, YP_001185848.1, YP_001188121.1, YP_001233688.1, YP_001268866.1, YP_001270391.1, YP_001345703.1, YP_001412573.1, YP_001417624.1, YP_001526058.1, YP_001579295.1, YP_001581170.1, YP_001668026.1, YP_001669478.1, YP_001671460.1, YP_001685569.1, YP_001747156.1, YP_001749732.1, YP_001765463.1, YP_001766294.1, YP_001790770.1, YP_001808775.1, YP_001809596.1, YP_001859758.1, YP_001888405.1, YP_001903233.1, YP_001977571.1, YP_002229759.1, YP_002231363.1, YP_002280472.1, YP_002297678.1, YP_002543874.1, YP_002549011.1, YP_002796201.1, YP_002801960.1, YP_002875335.1, YP_002897523.1, YP_002912290.1, YP_002974935.1, YP_003060891.1, YP_003264235.1, YP_003552364.1, YP_003578319.1, YP_003591946.1, YP_003607814.1, YP_003641922.1, YP_003674025.1, YP_003692877.1, YP_003755112.1, YP_003896973.1, YP_003907026.1, YP_003912421.1, YP_004086766.1, YP_004142571.1, YP_004147141.1, YP_004228105.1, YP_004278247.1, YP_004305252.1, YP_004356916.1, YP_004361407.1, YP_004378186.1, YP_004379856.1, YP_004390782.1, YP_004472442.1, YP_004590892.1, YP_004612414.1, YP_004676537.1, YP_004693233.1, YP_004701580.1, YP_004701637.1, YP_004704442.1, YP_108931.1, YP_110490.1, YP_168667.1, YP_237931.1, YP_260624.1, YP_262985.1, YP_271307.1, YP_276987.1, YP_334171.1, YP_337172.1, YP_350660.1, YP_351134.1, YP_364386.1, YP_366340.1, YP_369710.1, YP_370582.1, YP_426342.1, YP_440141.1, YP_442361.1, YP_468848.1, YP_521636.1, YP_554363.1, YP_608454.1, YP_610700.1, YP_614980.1, YP_622254.1, YP_625753.1, YP_680590.1, YP_751687.1, YP_767071.1, YP_774090.1, YP_774932.1, YP_788372.1, YP_858562.1, YP_928515.1, YP_983084.1, YP_995622.1, ZP_00948889.1, ZP_00954344.1, ZP_00959736.1, ZP_00998881.1, ZP_01011725.1, ZP_01037109.1, ZP_01058030.1, ZP_01076707.1, ZP_01103959.1, ZP_01167926.1, ZP_01224713.1, ZP_01442907.1, ZP_01446892.1, ZP_01550953.1, ZP_01625518.1, ZP_01745731.1, ZP_01750280.1, ZP_01754305.1, ZP_01763880.1, ZP_01769626.1, ZP_01865961.1, ZP_01881393.1, ZP_01901558.1, ZP_02145337.1, ZP_02151268.1, ZP_02152332.1, ZP_02167267.1, ZP_02190082.1, ZP_02242934.1, ZP_02360937.1, ZP_02367056.1, ZP_02385477.1, ZP_02456487.1, ZP_02883670.1, ZP_03263915.1, ZP_03263990.1, ZP_03400081.1, ZP_03452573.1, ZP_03456092.1, ZP_03517291.1, ZP_03529055.1, ZP_03571515.1, ZP_03572809.1, ZP_03587785.1, ZP_03588560.1, ZP_03697266.1, ZP_03697962.1, ZP_04521092.1, ZP_04590693.1, ZP_04890914.1, ZP_04891982.1, ZP_04893793.1, ZP_04902131.1, ZP_04905327.1, ZP_04941068.1, ZP_04944536.1, ZP_04945255.1, ZP_04959332.1, ZP_04964181.1, ZP_05053721.1, ZP_05063588.1, ZP_05073059.1, ZP_05077806.1, ZP_05082750.1, ZP_05091128.1, ZP_05095488.1, ZP_05101701.1, ZP_05116783.1, ZP_05121836.1, ZP_05127756.1, ZP_05637806.1, ZP_05742087.1, ZP_05783548.1, ZP_05786246.1, ZP_05843149.1, ZP_05945960.1, ZP_06459045.1, ZP_06487195.1, ZP_06492453.1, ZP_06493162.1, ZP_06703644.1, ZP_06731146.1, ZP_06839371.1, ZP_07007312.1, ZP_07266194.1, ZP_07374050.1, ZP_07662787.1, ZP_07778196.1, ZP_07797983.1, ZP_08099459.1, ZP_08138203.1, ZP_08141719.1, ZP_08142973.1, ZP_08177102.1, ZP_08185821.1, ZP_08186468.1, ZP_08208888.1, ZP_08266590.1, ZP_08402041.1, ZP_08406891.1, ZP_08522175.1, ZP_08527488.1, ZP_08631252.1, ZP_08636687 and variants thereof.

The fatty acid reductase used according to the invention and preferably also other enzymes used according to the invention are recombinant enzymes. In a preferred embodiment, the term "recombinant", as used herein, is understood to mean that the nucleic acid molecule encoding the corresponding enzyme does not occur in the natural cell and/or it has been produced using gene technology methods. In a preferred embodiment, the term recombinant protein is used if the corresponding polypeptide is encoded by a recombinant nucleic acid. In a preferred embodiment, a recombinant cell, as used herein, is understood to mean a cell which has at least one recombinant nucleic acid or recombinant polypeptide. Methods suitable for producing recombinant molecules or cells are known to the person skilled in the art, for example those described in Sambrook/Fritsch/Maniatis (1989): Molecular Cloning: A Laboratory Manual, Cold Spring Harbor Laboratory Press, 2nd edition. Recombinant enzymes are preferably overexpressed, for example by using pET or pGEX vector systems, which are known to the person skilled in the art.

With regard to the choice of organism, the whole-cell catalyst usable according to the invention is not subject to any restrictions, provided it is culturable, stable and amenable to possible modifications introducible by gene technology methods, for example methods for attenuating enzyme activities, an example being knock-outs. For instance, the cell can equally be a prokaryotic cell or eukaryotic cell. In the case of a eukaryotic cell, particular preference is given to unicellular eukaryotes, especially yeasts such as *Saccharomyces cerevisiae, Candida tropicalis, Candida albicans* and *Pichia pastoris*. In the case of prokaryotic cells, the cell can, for example, be a bacterium selected from the group comprising *Magnetococcus, Mariprofundus, Acetobacter, Acetobacterium, Acidiphilium, Afipia, Ahrensia, Asticcacaulis, Aurantimonas, Azorhizobium, Azospirillum, Bacillus, Bartonella, tribocorum, Beijerinckia, Bradyrhizobium, Brevundimonas, subvibrioides,*

Brucella, Caulobacter, Chelativorans, Citreicella, Citromicrobium, Clostridium, Corynebacterium, Dinoroseobacter, Erythrobacter, Fulvimarina, Gluconacetobacter, Granulibacter, Hirschia, Hoeflea, Hyphomicrobium, Hyphomonas, Ketogulonicigenium, Labrenzia, Loktanella, Magnetospirillum, Maricaulis, Maritimibacter, Mesorhizobium, Methylobacterium, Methylocystis, Methylosinus, Nitrobacter, Novosphingobium, Oceanibulbus, Oceanicaulis, Oceanicola, Ochrobactrum, Octadecabacter, Oligotropha, Paracoccus, Parvibaculum, Parvularcula, Pelagibaca, Phaeobacter, Phenylobacterium, Polymorphum, Pseudovibrio, Rhodobacter, Rhodomicrobium, Rhodopseudomonas, Rhodospirillum, Roseibium, Roseobacter, Roseomonas, Roseovarius, Ruegeria, Sagittula, Silicibacter, Sphingobium, Sphingomonas, Sphingopyxis, Starkeya, Sulfitobacter, Thalassiobium, Xanthobacter, Zymomonas, Agrobacterium, Rhizobium, Sinorhizobium, Anaplasma, Ehrlichia, Neorickettsia, Orientia, Rickettsia, Wolbachia, Bordetella, Burkholderia, Cupriavidus, Taiwanensis, Lautropia, Limnobacter, Polynucleobacter, Ralstonia, Chromobacterium, Eikenella, corrodens, Basfia, Kingella, Laribacter, Lutiella, Neisseria, Simonsiella, Achromobacter, Acidovorax, Alicycliphilus, Aromatoleum, Azoarcus, Comamonas, Dechloromonas, Delftia, Gallionella, Herbaspirillum, Herminiimonas, Hylemonella, Janthinobacterium, Leptothrix, Methylibium, Methylobacillus, Methylophilales, Methyloversatilis, Methylovorus, Nitrosomonas, Nitrosospira, Oxalobacter, Parasutterella, Polaromonas, Polaromonas, Pusillimonas, Rhodoferax, Rubrivivax, Sideroxydans, Sutterella, wadsworthensis, Taylorella, Thauera, Thiobacillus, Thiomonas, Variovorax, Verminephrobacter, Anaeromyxobacter, Bdellovibrio, bacteriovorus, Bilophila, Desulfarculus, Desulfatibacillum, Desulfobacca, Desulfobacterium, Desulfobulbus, Desulfococcus, Desulfohalobium, Desulfitobacterium, Desulfomicrobium, Desulfonatronospira, Desulfotalea, Desulfovibrio, Desulfuromonas, Geobacter, Haliangium, Hippea, Lawsonia, Myxococcus, Pelobacter, Plesiocystis, Sorangium, Stigmatella, Syntrophobacter, Syntrophus, Arcobacter, Caminibacter, Campylobacter, Helicobacter, Nitratifractor, Nitratiruptor, Sulfuricurvum, Sulfurimonas, Sulfurospirillum, Sulfurovum, Wolinella, Buchnera, Blochmannia, Hamiltonella, Regiella, Riesia, Citrobacter, Cronobacter, Dickeya, Edwardsiella, Enterobacter, Erwinia, Escherichia, Klebsiella, Pantoea, Pectobacterium, Proteus, Providencia, Rahnella, Salmonella, Serratia, Shigella, Sodalis, Wigglesworthia, Glossina, Xenorhabdus, Yersinia, Acidithiobacillus, Acinetobacter, Aeromonas, Alcanivorax, Alkalilimnicola, Allochromatium, Afteromonadales, Alteromonas, Baumannia, Beggiatoa, Bermanella, Carsonella, Ruthia, Vesicomyosocius, Cardiobacterium, Chromohalobacter, Colwellia, Congregibacter, Coxiella, Dichelobacter, Endoriftia, Enhydrobacter, Ferrimonas, Francisella, Glaciecola, Hahella, Halomonas, Halorhodospira, Halothiobacillus, Idiomarina, Kangiella, Legionella, Marinobacter, Marinomonas, Methylobacter, Methylococcus, Methylomicrobium, Methylophaga, Moraxella, Moritella, Neptuniibacter, Nitrococcus, Pseudoalteromonas, Psychrobacter, Psychromonas, Reinekea, Rickettsiella, Saccharophagus, Shewanella, Succinatimonas, Teredinibacter, Thioalkalimicrobium, Thioalkalivibrio, Thiomicrospira, Tolumonas, Vibrionales, Actinobacillus, Aggregatibacter, Gallibacterium, Haemophilus, Histophilus, Mannheimia, Pasteurella, Azotobacter, Cellvibrio, Pseudomonas, Affivibrio, Grimontia, Photobacterium, Photobacterium, Vibrio, Pseudoxanthomonas, Stenotrophomonas, Xanthomonas, Xylella, Borrelia, Brachyspira, Leptospira, Spirochaeta, Treponema, Hodgkinia, Puniceispirillum, Liberibacter, Pelagibacter, Odyssella, Accumulibacter, more particularly B. subtilis, B. megaterium, C. glutamicum, E. coli, Pseudomonas sp., Pseudomonas fluorescens, Pseudomonas putida, Pseudomonas stutzeri, Acinetobacter sp., Burkholderia sp., Burkholderia thailandensis, cyanobacteria, Klebsiella sp., Klebsiella oxytoca, Salmonella sp., Rhizobium sp. and Rhizobium meliloti. In a particularly preferred embodiment, the cell is an enterobacterium, most preferably Escherichia coli.

It is advantageous when the whole-cell catalyst according to the invention comprises not only the fatty acid reductase, phosphopantetheinyl transferase and the transaminase, but also an alanine dehydrogenase in order to regenerate from inorganic nitrogen-containing molecules the alanine consumed by the transaminase during the amination of the terminal aldehyde group. In a preferred embodiment, the term "alanine dehydrogenase", as used herein, is understood to mean an enzyme which catalyzes the conversion of L-alanine with consumption of water and $NAD^+$ to pyruvate, ammonia and NADH and the reverse reaction. In a particularly preferred embodiment, the alanine dehydrogenase is selected from the group of alanine dehydrogenases comprising the amino acid sequence of the alanine dehydrogenase from Bacillus subtilis (database code L20916), Rhizobium leguminosarum (database code CP001622), Vibrio proteolyticus (database code AF070716), Mycobacterium tuberculosis (database code X63069), Enterobacter aerogenes (database code AB013821), EGR93259.1, YP_003654745.1, YP_003651439.1, YP_003637111.1, YP_003631815.1, YP_001327051.1, YP_001262560.1, YP_886996.1, YP_882850.1, YP_704410.1, YP_703508.1, ZP_08624689.1, YP_001230376.1, P17557.1, P17556.1, CCB94892.1, CCB73698.1, YP_001168635.1, YP_004668736.1, YP_004569425.1, YP_003513168.1, YP_004561169.1, ZP_08554945.1, YP_400777.1, ZP_08311476.1, ZP_08310170.1, ZP_08267322.1, ZP_08263846.1, ZP_07898723.1, YP_149301.1, YP_148605.1, YP_004340432.1, EFT09946.1, EFS80513.1, EFS51332.1, EFS42459.1, YP_003060895.1, YP_003059033.1, ZP_03305373.1, YP_847214.1, YP_004095847.1, YP_003338282.1, YP_003337256.1, YP_355846.1, YP_253131.1, ZP_08197563.1, ZP_08196283.1, ADW06447.1, YP_734091.1, NP_372233.1, NP_102173.1, ZP_08170259.1, EGD36706.1, EGD32748.1, ZP_08155540.1, YP_004142849.1, YP_002417649.1, YP_001301040.1, YP_002992892.1, YP_081348.1, YP_080482.1, YP_002476349.1, ZP_08115025.1, ZP_08114403.1, YP_003552869.1, YP_002358112.1, YP_575010.1, YP_477594.1, YP_474564.1, YP_130399.1, YP_129373.1, YP_123314.1, NP_810467.1, NP_646469.1, NP_626044.1, NP_391071.1 (encoded by SEQ ID NO: 11), ZP_08086822.1, ZP_08084776.1, ZP_08083119.1, ZP_08020768.1, ZP_08013590.1, ZP_08011832.1, YP_003783744.1, YP_002781576.1, YP_002780533.1, ZP_02195873.1, NP_797482.1, ZP_07645051.1, ZP_07643260.1, ZP_06611917.1, AAT40119.1, ZP_07864946.1, YP_004068409.1, YP_002796203.1, YP_002774420.1, YP_003600348.1, YP_003599946.1, YP_003565624.1, YP_003565223.1, YP_335198.1, YP_423850.1, YP_155059.1, ZP_07843538.1, ZP_07841226.1, ZP_06928932.1, ZP_05692073.1, ZP_05687006.1, ZP_04867480.1, YP_775531.1, CBE70214.1, ZP_07721182.1, ZP_04302850.1, ZP_04298961.1, ZP_04287684.1, ZP_04277177.1, ZP_04248389.1, ZP_04235899.1, ZP_02159718.1, ZP_02152178.1, YP_003974610.1, YP_003546595.1, YP_002317127.1, ZP_07313778.1, ZP_07302778.1, ZP_07298850.1, CBK69442.1, YP_003413835.1, YP_003595089.1, ZP_06807811.1, YP_003582455.1, YP_003464731.1, YP_003496397.1, YP_003421918.1, CBL07274.1, CBK64956.1, YP_003508515.1, AAL87460.1, AAC23579.1, AAC23578.1, AAC23577.1, ACU78652.1, YP_003471439.1, YP_003452777.1, ZP_06384971.1, ACY25368.1, ABC26869.1, AAP44334.1, EEZ80018.1, ZP_05110458.1, 1PJB_A, ZP_04717201.1, ZP_04689103.1, CAO90307.1, CAM75354.1, CAA44791.1, BAA77513.1, EGR96638.1, EGL90046.1, YP_004510847.1, ZP_08450330.1, YP_003387804.1, YP_003058152.1, EFS74272.1, EFS67128.1, ZP_06844564.1, YP_826658.1, YP_001195249.1, YP_003095978.1, YP_469292.1, YP_004442054.1, YP_004461174.1, YP_004055616.1, YP_003576656.1, YP_003094537.1, YP_001295973.1, AEE71143.1, YP_004447480.1, YP_003761844.1, YP_040853.1, YP_003154888.1, YP_003142045.1, YP_002280953.1, NP_371963.1, NP_422368.1, EGC98966.1, EGC76398.1, YP_004263661.1, YP_004252039.1, YP_679036.1, YP_499973.1, ZP_08054972.1, ZP_08053009.1, ZP_04067276.1, ZP_03968868.1, ZP_03963857.1, ZP_03933079.1, ZP_03497046.1, ZP_06668924.1, ZP_06667106.1, ZP_06324464.1, ZP_06196777.1, ZP_05114159.1, ZP_05083968.1, ZP_05070370.1, ZP_05030022.1, ZP_04673064.1, ZP_03517011.1, ZP_03505783.1, XP_001310698.1, ABK27691.1 and CAB59281.2 and variants thereof. For the reaction catalysed by the alanine dehydrogenase, the presence is required of not only pyruvate, which is formed as part of the primary metabolism of any cell suitable as whole-cell catalyst, but also ammonium. The latter is typically provided in the form of inorganic nitrogen salts, for example ammonium salts, nitrates or the like. Preferably, an ammonium salt, for example ammonium chloride, is added to the aqueous reaction medium.

Furthermore, it is advantageous when the whole-cell catalyst according to the invention expresses an alkane hydroxylase and optionally further enzymes essential for the activity of the alkane hydroxylase, especially when a fatty acid having only one terminal carboxy function is used as substrate for producing a diamine. The alkane hydroxylase and/or an additionally expressed alcohol dehydrogenase oxidize the terminal carbon atom then up to the aldehyde group, which can subsequently be aminated by the transaminase, or up to the carboxyl group, which is converted by an α-dioxygenase or the combination of fatty acid reductase and a phosphopantetheinyl transferase to a terminal aldehyde group, which can subsequently be aminated by the transaminase. In a preferred embodiment, the term "alkane hydroxylase", as used herein, is understood to mean an enzyme which catalyzes the hydroxylation of unsubstituted linear alkyl radicals comprising at least six, preferably twelve, carbon atoms.

According to the invention, numerous oxidation systems, as described in, inter alia, PCT/EP 2008/067447, are suitable as alkane hydroxylases. In a preferred embodiment, the alkane hydroxylase is a cytochrome P450 monooxygenase of the CYP153 family. In a preferred embodiment, the term "cytochrome P450 monooxygenase of the CYP153 family" is understood to mean a cytosolic oxidase which is part of a 3-component system which further comprises a ferredoxin and a ferredoxin reductase, with an alkane binding site and the ability to hydroxylate alkanes. In a particularly preferred embodiment, it is an enzyme which has to at least 80, preferably 90, most preferably 95 or 99%, sequence identity to the cytochrome P450 monooxygenase of the CYP153 family from *Alcanivorax borkumensis* SK2 (database code YP_691921) or an enzyme which comprises a polypeptide sequence which has at least 80, preferably 90, most preferably 95 or 99%, sequence identity to the cytochrome P450 monooxygenase of the CYP153 family from *Alcanivorax borkumensis* SK2 (database code YP_691921) and moreover has alkane hydroxylase activity. As throughout this application, the stated database codes concern the NCBI (National Center for Biotechnology Information, Bethesda, USA) databases, specifically the version available online on 21 Nov. 2012. In a preferred embodiment, the term "cytochrome P450 monooxygenase of the CYP153 family" is understood to mean a non-membrane-bound oxidase which includes a binding site for alkanes, unsubstituted linear alkyl radicals comprising at least five, preferably twelve, carbon atoms or monohydroxylated alkanes and the polypeptide chain of which comprises the motif LL(I/L)(V/I)GGNDTTRN. In a preferred embodiment, a "cytochrome P450 monooxygenase of the CYP153 family", as used herein, is a cytochrome P450 monooxygenase of the CYP153 family from *Alcanivorax borkumensis* SK2 (database code YP_691921) or a variant thereof which preferably has alkane hydroxylase activity.

For the optimal supply of the cytochrome P450 monooxygenase of the CYP153 family with electrons from the reducing agent, preferably NADH, it is preferred that the cell the alkane hydroxylase is expressed together with ferredoxin reductase that interacts functionally with it and ferredoxin that interacts functionally with it. These may be isolated polypeptides or, in the case of using a whole-cell catalyst, coexpressed polypeptides or polypeptides fused on the N- or C-terminus with the cytochrome P450 monooxygenase of the CYP153 family. Whether a ferredoxin reductase or a ferredoxin interact functionally with a given cytochrome P450 monooxygenase of the CYP153 family with one another can be readily established by the person skilled in the art by whether the reducing agent is oxidized more efficiently in the presence of an alkane substrate and the three polypeptides than when at least one of the three is absent. Alternatively, it is possible to use the enzyme assay described by Scheps, D., Malca, H., Hoffmann, B., Nestl, B. M, and Hauer, B. (2011) *Org. Biomol. Chem.*, 9, 6727, which, in the case of functionally interacting polypeptides, exhibits a considerable increase in the reaction rate. In a particularly preferred embodiment, the cytochrome P450 monooxygenase of the CYP153 family, the ferredoxin and the ferredoxin reductase originate from the same organism. In a particularly preferred embodiment, they are the ferredoxin reductase from *Alcanivorax borkumensis* SK2 (database code YP_691923) or a variant thereof, the ferredoxin from *Alcanivorax borkumensis* SK2 (database code YP_691920) or a variant thereof and the cytochrome P450 monooxygenase of the CYP153 family from *Alcanivorax borkumensis* SK2 (database code YP_691921) or a variant thereof.

In a further preferred embodiment, the alkane hydroxylase is an AlkB monooxygenase. AlkB represents an oxidoreductase which initially became known from the AlkBGT system of *Pseudomonas putida* Gpo1, and which is dependent on two further polypeptides, AlkG and AlkT. AlkT is characterized as a FAD-dependent rubredoxin reductase, which transfers electrons from NADH to AlkG. AlkG is a rubredoxin, an iron-containing redox protein which functions as a direct electron donor to AlkB. In a preferred embodiment, the term "AlkB monooxygenase" is a polypeptide having a sequence homology of at least 75, 80, 85, 90, 92, 94, 96, 98 or 99%—specified in order of increasing preference—to the sequence of the AlkB of *Pseudomonas putida* Gpo1 (database code: CAB54050.1; this database code originates like all others from the prior art used in the application, namely from the NCBI database, more precisely the release available online on 15 Oct. 2012) having the capability to oxidize alkanes. In a particularly preferred embodiment, the AlkB monooxygenase is an oxidoreductase which functionally interacts with the AlkG (CAB54052.1) and AlkT (CAB54063.1) polypeptides from *Pseudomonas putida* Gpo1 and oxidizes alkanes. For the optimal supply of the AlkB alkane hydroxylase with electrons, it is preferred that the cell the alkane hydroxylase is expressed together with auxiliary proteins that interact functionally with it, preferably AlkG and/or AlkT or variants of each, and in a particularly preferred embodiment they are again AlkG (CAB54052.1) and AlkT (CAB54063.1) polypeptides from *Pseudomonas putida* Gpo1.

When using a whole-cell catalyst, the problem can arise that a substrate has to be brought into contact with an intracellularly localized enzyme so that it results in the desired reaction. In the case of long-chain alkanes and derivatives thereof, it is preferred that the whole-cell catalyst has a polypeptide of the AlkL family. AlkL is a membrane protein from *Pseudomonas putida*, which protein can import long-chain fatty acids and derivatives thereof into bacterial cells. In a preferred embodiment, a "polypeptide of the AlkL family", as used herein is a polypeptide which, over a length of 230 successive amino acids, has an at least 80, preferably 90, more preferably 90% sequence identity to AlkL from *Pseudomonas putida* (database code CAB69081) or a variant of AlkL from *Pseudomonas putida* and preferably the ability to assist the import of long-chain alkanes into the inside of a cell. In a further embodiment, a "polypeptide of the AlkL family", as used herein, is a polypeptide located in the outer membrane of a Gram-negative bacterium and which has the sequence motif DXWAPAXQ(V/A)GXR, where X is a proteinogenic amino acid, and preferably is additionally AlkL from *Pseudomonas putida* (database code CAB69081) or a variant thereof. Examples of members of the AlkL family include AlkL from *Pseudomonas putida* (database code CAB69081), *Marinobacter aquaeolei* VT8 (database code YP_957722), *Oceanicaulis alexandrii* HTCC2633 (database code ZP_00953584), *Marinobacter manganoxydans* Mnl7-9 (database code ZP_09158756), *Caulobacter* sp. K31 (database code YP_001672217), *Pseudomonas oleovorans* (database code Q00595) and variants thereof.

The teaching of the present invention can be carried out by not only using macromolecules having the exact amino acid or nucleic acid sequence to which reference is made herein or by not only using a cell having reduced activity, relative to the respective wild type, of a polypeptide having the exact amino acid sequence to which reference is made herein, but also by using a variant of such macromolecules or a cell having a reduced activity, relative to the respective wild type of the respective cell, of a variant of the polypeptide, which variant can be obtained by deletion, addition or substitution of one or more than one amino acid or nucleic acid. In a preferred embodiment, the term "variant" of a nucleic acid sequence or amino acid sequence, used hereinafter synonymously and exchangeably with the term "homologue", as used herein, means another nucleic acid or amino acid sequence comprising or representing a sequence which, with respect to the corresponding original wild-type nucleic acid or amino acid sequence, has a homology, used here synonymously with identity, of 70, 75, 80, 85, 90, 92, 94, 96, 98, 99% or greater, wherein preferably amino acids other than the ones forming the catalytically active site or essential for the structure or folding are deleted or substituted or are merely conservatively substituted, for example a glutamate instead of an aspartate or a leucine instead of a valine. The prior art describes algorithms, which may be used to calculate the degree of homology of two sequences, e.g. Arthur Lesk (2008), Introduction to Bioinformatics, $3^{rd}$ edition. In a further more preferred embodiment of the present invention, the variant of an amino acid or nucleic acid sequence, preferably in addition to the sequence homology mentioned above, has substantially the same enzymatic activity of the wild-type molecule and/or of the original molecule. For example, a variant of an enzymatically active polypeptide protease has the same, or substantially the same, proteolytic activity as the polypeptide enzyme, i.e. the capability to catalyse the hydrolysis of a peptide bond. In a particular embodiment, the term "substantially the same enzymatic activity" means an activity, with respect to the substrates of the wild-type polypeptide, which clearly lies above the background activity or/and differs from the $K_M$ and/or $k_{cat}$ values by less than 3, more preferably 2, even more preferably one order of magnitude, which the wild-type polypeptide exhibits with respect to the same substrates. In a further preferred embodiment, the term "variant" of a nucleic acid or amino acid sequence includes at least one active part or fragment of the nucleic acid or amino acid sequence. In a further preferred embodiment, the term "active part", as used herein, means an amino acid sequence or a nucleic acid sequence which has a smaller amino acid sequence than the full length of the amino acid sequence or encodes a smaller amino acid sequence than the full length of the amino acid sequence, where the amino acid sequence or the encoded amino acid sequence with the smaller length than the wild-type amino acid sequence has substantially the same enzymatic activity as the wild-type polypeptide or a variant thereof, for example as protease. In a particular embodiment, the term "variant" of a nucleic acid encompasses a nucleic acid, the complementary strand of which, preferably under stringent conditions, binds to the wild-type nucleic acid. The stringency of the hybridization reaction is readily determinable by those skilled in the art and depends in general on the length of the probe, the washing temperatures and the salt concentration. Generally, longer probes require higher temperatures for the hybridization, whereas shorter probes work at lower temperatures. Whether hybridization takes place depends in general on the capability of the denatured DNA to anneal to complementary strands which are present in its environment, specifically below the melting temperature. The stringency of hybridization reaction and corresponding conditions are described in more detail in F M Ausubel (1995), Current Protocols in Molecular Biology. John Wiley & Sons, Inc. Instructions for identifying DNA sequences by means of hybridization can be found by the person skilled in the art inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place in a preferred embodiment under stringent conditions, i.e. only hybrids are formed in which probe and target sequence, i.e. the polynucleotides treated with the probe, are at least 70% identical. It is known that the stringency of the hybridization including the washing steps is influenced and/or determined by varying the buffer composition, the temperature and the salt concentration. The hybridization reaction is generally carried out at a relatively low stringency compared with the washing steps (Hybaid Hybridisation Guide, Hybaid Limited, Teddington, UK, 1996). For the hybridization reaction, for example, a buffer corresponding to 5×SSC buffer can be used at a temperature of about 50° C.-68° C. In this connection, probes can also hybridize to polynucleotides which have less than 70% identity to the sequence of the probe. Such hybrids are less stable and are removed by washing under stringent conditions. This can be achieved for example by lowering the salt concentration to 2×SSC and optionally subsequently 0.5× SSC (The DIG System User's Guide for Filter Hybridisation, Boehringer Mannheim, Mannheim, Germany, 1995), in which case a temperature of, increasing in order of preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. is established. Temperature ranges from about 64° C.-68° C. or about 66° C.-68° C. are preferred. It is optionally possible to reduce the salt concentration down to a concentration corresponding to 0.2×SSC or 0.1×SSC. By means of a stepwise increase in the hybridization temperature in steps of about 1-2° C. from 50° C. to 68° C., polynucleotide fragments can be isolated which, for example in the order of increasing preference, have at least 70% or at least 80% or at least 90%, at least 91%, at least 92%, at least 93%, at least 94%, at least 95%, at least 96%, at least 97%, at least 98% or at least 99% identity to the sequence of the nucleic acid molecule used. Further instructions relating to the hybridization are commercially available in the form of so-called kits (e.g. DIG Easy Hyb from Roche Diagnostics GmbH, Mannheim, Germany, Catalogue No. 1603558). In a preferred embodiment, the term "variant" of a nucleic acid, as used herein, encompasses any nucleic acid sequence which encodes the same amino acid sequence as the original nucleic acid or a variant of this amino acid sequence in the context of the degeneracy of the genetic code.

In a preferred embodiment, the cell used according to the invention has a reduced activity, with respect to its wild type, of at least one enzyme which catalyses one of the reactions of the β-oxidation of fatty acids, and preferably this is an enzyme from the group comprising fatty acid-CoA ligase, acyl-CoA dehydrogenase, 2,4-dienoyl-CoA reductase, enoyl-CoA hydratase and 3-ketoacyl-CoA thiolase, a fatty acid importer or variants thereof. The β-oxidation of fatty acids is a widespread metabolic pathway which equally permits prokaryotic and eukaryotic organisms to oxidize fatty acids and to make the chemical energy present therein available to metabolism. In the broader sense, it starts with the uptake of a fatty acid into the cell. There, if the conditions require it, the fatty acid is firstly oxidized at the β-position of the CoA-fatty acid ester by an acyl-CoA dehydrogenase, in the case of E. coli FadE. A similar molecule can alternatively also be formed from a double-unsaturated fatty acid by reduction by means of a 2,4-dienoyl-CoA reductase, in the case of E. coli FadH. A multifunctional enzyme, the enoyl-CoA hydratase/3-hydroxyacyl-CoA dehydrogenase, in the case of E. coli FadB, then catalyzes the hydration with the formation of the secondary alcohol and its subsequent oxidation to the ketone. In the last step, a 3-ketoacyl-CoA thiolase, in the case of E. coli FadA, catalyzes the cleavage of the ketoacyl-CoA, with the result that acetyl-CoA and a CoA ester of the fatty acid that is two carbon atoms shorter compared to the starting molecule are released. If the latter is not likewise acetyl-CoA, it can be fed again into the β-oxidation cycle and be shortened via oxidation. Also involved in the regulation of the β-oxidation of fatty acids is FadR, a regulator of the Fad operon, which includes the genes required for the degradation of fatty acids, without FadR appearing to catalyse a reaction of the β-oxidation. In a preferred embodiment, the term "enzyme which catalyzes one of the reactions of the β-oxidation of fatty acids" is understood as meaning any enzyme which interacts directly with the fatty acid substrate or a molecule formed therefrom on the pathway to the acetyl-CoA, preferably recognizes it as substrate, and catalyzes its conversion to a metabolic product lying closer to the acetyl-CoA on this degradation pathway, preferably including the fatty acid importer, which effects the uptake of the fatty acid into the cell. For example, according to the preceding definition, these enzymes include acyl-CoA dehydrogenase, since it interacts with the fatty acid-CoA ester and catalyzes its conversion to the enyol-CoA, which lies closer to the acetyl-CoA on the metabolic pathway of β-oxidation than the fatty acid-CoA ester. In a particularly preferred embodiment, the term "enzyme which catalyzes one of the reactions of the β-oxidation of fatty acids", as used herein, is understood as meaning any enzyme from the group which comprises the gene products FadA, FadB, FadD, FadL and FadE from E. coli and/or their variants or homologues from other organisms. The gene products FadA, FadB, FadD, FadL and FadE from E. coli as well as variants and homologues from numerous other biotechnologically useful organisms and their nucleic acid and polypeptide sequences are described in the prior art, for example FadA under accession number AP009048.1, FadB under accession number BAE77457.1, FadD under accession number BAA15609.1, and FadE under accession number BAA77891.2. The prior art discloses numerous assays which are suitable specifically for measuring the activity of enzymes which catalyse one of the reactions of the β-oxidation of fatty acids, for example in K Kameda & W D Nunn (1981) J. Biol. Chem. 256, 5702-5707, Hi Marrakchi, W E DeWolf, C Quinn, J West, B J Polizzi, C Y So et al. (2003) Biochem. J. 370, 1055-1062, Lobo et al. (2001) and X Yu, T Liu, F Zhu, and C Khosla (2011) PNAS, electronic publication prior to print.

For the efficiency of the whole-cell catalyst according to the invention, it is advantageous when the substrate to be converted, preferably the carboxylic acid or dicarboxylic acid or a monoester thereof, can easily enter into contact with the enzymes which are required according to the invention and which are located inside the whole-cell catalyst. Therefore, it is critical that the substrate can reach the interior of the cell. To facilitate this, it is preferred that the whole-cell catalyst expresses a fatty acid importer, in the case of a bacterial, more particularly Gram-negative, whole-cell catalyst, particularly preferably the fatty acid importer FadL (database code: BAA16205.1) or a variant, preferably in a concentration and with an activity which is increased with respect to the activity of the wild type of the corresponding whole-cell catalyst. Increasing the activity of a polypeptide with respect to the wild type of the cell can be achieved via various routes routinely accessible to the person skilled in the art, for example the incorporation of additional copies, functionally linked to a promoter, of the nucleotide sequence encoding the polypeptide or the exchange of the natural promoter for a stronger promoter.

It has been found that, according to the invention, the amines and diamines are produced in a higher yield and purity when the background of enzymes expressed endogenously in the whole-cell catalyst is optimized in such a way to reduce or switch off the activity of endogenous enzymes which degrade reactants, intermediates or products of the process according to the invention or using the cell according to the invention, preferably methyl esters of ω-aminocarboxylic acids, ω-hydroxycarboxlic acids, ω-oxocarboxylic acids and dicarboxylic acids, on metabolic pathways or otherwise modify them, leading away from the development of the desired product. Against this background, it may be advantageous when the whole-cell catalyst according to the invention is a cell having, with respect to its wild type, a reduced activity of the esterase BioH [database code YP_492020.1] or a variant thereof. Such cells having reduced BioH activity, the production thereof and assays to determine activity are described in the European patent application EP 12007663.3.

If the carboxylic acid, dicarboxylic acid or monoester thereof used are mixtures of compounds in which the terminal carboxy groups are present to a high degree, preferably to an extent of at least 50, 60, 70, 80, 90, 95 or 99%, in the form of an ester, for example because of the better availability of these substrates or the toxicity of free carboxylic acids or dicarboxylic acids, the monoester can be provided by partial or complete hydrolysis of completely esterified dicarboxylic acids and the free carboxylic acid by partial or complete hydrolysis of completely esterified carboxylic acids. In this case, it is advantageous to increase the capacity of the cell in relation to ester hydrolysis by overexpression of a suitable esterase. To this end, in a preferred embodiment, the activity of the ester hydrolase BioH or a variant thereof is increased with respect to the wild type of the whole-cell catalyst used, particularly preferably by overexpression. The corresponding monoester and/or the unesterified carboxylic acid or dicarboxylic acid is then provided in situ by ester hydrolysis. The partial or complete hydrolysis of a completely esterified dicarboxylic acid can also be effected by chemically catalysed hydrolysis, for example at low pH levels.

The whole-cell catalyst according to the invention can be preferably used in a process for converting a carboxylic acid or dicarboxylic acid or a monoester thereof to the corresponding amine or diamine, wherein the carboxylic acid or dicarboxylic acid or the monoester thereof is a compound of the formula (I)

$$R^1\text{-A-COOR}^2 \qquad (I),$$

where $R^1$ is selected from the group comprising —H and $COOR^3$, where $R^2$ and $R^3$ are each independently selected from the group comprising H, methyl, ethyl and propyl, with the proviso that at least one of the radicals $R^2$ and $R^3$ is H, where A is an unbranched, branched, linear, cyclic, substituted or unsubstituted hydrocarbon group having at least four carbon atoms. In a preferred embodiment, A is a structure of the formula —$(CH_2)_n$—, where n is preferably 4, 5, 6, 7, 8, 9, 10, 11, 12, 13, 14, 15, 16, 17, 18, 19, 20, 21, 22, 23, 24, 25, 26, 27, 28, 29 or 30. In a preferred embodiment, the carboxylic acid or dicarboxylic acid is lauric acid or ω-carboxylauric acid. In a further most preferred embodiment, the carboxylic acid is a carboxylic acid of the formula $CH_3$—$(CH_2)_n$—COOH, where n is preferably 4, 5, 6, 7, 8, 9, 10, 11, 12, 13, 14, 15, 16, 17, 18, 19, 20, 21, 22, 23, 24, 25, 26, 27, 28, 29 or 30, preferably hexanoic acid or decanoic acid. In a further most preferred embodiment, the carboxylic acid or dicarboxylic acid is a dicarboxylic acid of the formula HOOC—$(CH_2)_n$—COOH, where n is preferably 4, 5, 6, 7, 8, 9, 10, 11, 12, 13, 14, 15, 16, 17, 18, 19, 20, 21, 22, 23, 24, 25, 26, 27, 28, 29 or 30, preferably ω-carboxyhexanoic acid or ω-carboxydecanoic acid. In a further most preferred embodiment, the carboxylic acid or dicarboxylic acid is ω-carboxytetradecanoic acid. Accordingly, the amine or diamine produced according to the invention is preferably a compound of the formula $CH_3$—$(CH_2)_n$—$NH_2$ or $NH_2$—$(CH_2)_n$—$NH_2$, where n is in each case preferably 4, 5, 6, 7, 8, 9, 10, 11, 12, 13, 14, 15, 16, 17, 18, 19, 20, 21, 22, 23, 24, 25, 26, 27, 28, 29 or 30.

With respect to the carboxylic acid or dicarboxylic acid or the monoester thereof and to any chemical compound described in this application, it is the case that the respective specified formula encompasses all salts, protonated or deprotonated, of the respective compound. For example, the lauric acid encompasses not only the protonated form, but also the salt laureate with all cations, for example sodium laureate.

It is a requirement of the process according to the invention that the enzymes used for the process according to the invention, optionally provided in the form of the whole-cell catalyst according to the invention, be contacted with the carboxylic acid or dicarboxylic acid or the monoester thereof in an aqueous solution. In a preferred embodiment, the term "contacting", as used herein, is understood to mean that the particular enzyme gets into direct contact with its substrate, more particularly without physical barriers such as impermeable membranes or the like being interposed. In the simplest case, contacting occurs by the substrate being added to an aqueous solution in which the enzyme or the whole-cell catalyst is situated.

Suitable for carrying out the teaching according to the invention is a reaction mixture comprising the whole-cell catalyst 8 according to the invention in aqueous solution and a carboxylic acid or dicarboxylic acid or a monoester thereof of the formula (I), where $R^1$ is selected from the group comprising —H $COOR^3$, where $R^2$ and $R^3$ are each independently selected from the group comprising H, methyl, ethyl and propyl, with the proviso that at least one of the radicals $R^2$ and $R^3$ is H, where A is an unbranched, branched, linear, cyclic, substituted or unsubstituted hydrocarbon group having at least four carbons, preferably the formula —$(CH_2)_n$—, where n is at least 4, particularly preferably at least 10. The aqueous solution must, for example with respect to composition, pH and temperature, be of such a nature that said solution supports, at least for a certain period, the viability or at least the catalytic capability of the whole-cell catalyst. The person skilled in the art knows numerous aqueous culture media which are suitable as aqueous solution and which are suitable for maintaining or culturing cells, more particularly cells of biotechnological importance. These include, equally, complete media such as LB media, minimal media such as M9 media and also selective media, for example those which have a high salt concentration and therefore only permit the growth of halophilic or at least halotolerant organisms. In a preferred embodiment, the term "aqueous culture medium", as used herein, is understood to mean a water-based reaction medium which, with respect to all relevant factors, in particular pH, salt content and temperature, is of such a nature that it maintains or promotes the viability of cells present therein, preferably microorganisms, and both aqueous culture medium and hydrophobic organic phase are present in liquid form. The temperature requirements of various biotechnologically important cells can be found in microbiology and molecular biology textbooks, for example Fuchs/Schlegel, 2008. In a preferred embodiment, the pH of the aqueous culture medium at the time point of contacting is between 4 and 9, more preferably between 4.5 and 8.5, most preferably between 6.5 and 7.5. In a further preferred embodiment, the temperature is between 0 and 45° C., more preferably between 15 and 40° C., most preferably between 20 and 37° C. The reaction mixture is typically present in a fermenter. Any reaction vessel which can be sterilized, preferably autoclaved, and allows the culturing of the whole-cell catalyst, aeration and control of the reaction conditions, for example the oxygen content and the temperature, can act as fermenter.

In a preferred embodiment, the reaction mixture comprises, in addition to the aqueous solution, a hydrophobic organic phase. This can comprise an organic solvent and/or a hydrophobic liquid cation exchanger for removing the ω-amino fatty acid from the aqueous solution. Suitable solvents and cation exchangers are described in EP11191520.3.

The present invention is more particularly described by the following FIGURES and non-limiting examples from which further features, embodiments, aspects and advantages of the present invention may be discerned.

FIG. 1: Detection of monoamines and diamines in the fermentation broth of the strain E. coli W3110 pACYC{Placuv5}[carA_Ms-npt_Noc]/pJ281_alaDH_B.s._TA_C.v.(ct) after a 21.75 h process time.

EXAMPLE 1

Producing an Expression Vector for the Expression of the Genes MSMEG_2956 from Mycobacterium smegmatis and npt from Nocardia sp.

To produce vectors for the coexpression of MSMEG_2956 (carA, SEQ ID No. 1) from Mycobacterium smegmatis encoding a fatty acid reductase (YP_887275.1) and with npt (SEQ ID No. 2) from Nocardia sp. encoding a phosphopantetheinyl transferase (AB183656.1) which phosphopantetheinylates the fatty acid reductase, both genes were amplified by means of PCR with insertion of homologous regions for recombinant cloning. In this connection, genomic DNA from the donor organism for the amplification of the gene MSMEG_2956 and a synthesized DNA fragment for the amplification of the gene npt served as template. The genes are under the control of a lacuv5 promoter (SEQ ID No. 3), which was likewise amplified by means of PCR proceeding from an available vector with insertion of homologous regions for the recombinant cloning.

In this connection, the following oligonucleotides were used:

```
Plac_H1_fw:
                                       (SEQ ID Nr. 4)
5'-TTATGCGACTCCTGCTGGCTATGGTGGGATTTCC-3'

Plac_H2_rv:
                                       (SEQ ID Nr. 5)
5'-GATCGTCATATGCCACTCTCCTTGGTTCC-3' carA_H2_fw:
                                       (SEQ ID Nr. 6)
5'-TGGCATATGACGATCGAAACGCGCG-3' carA_H3_rv:
                                       (SEQ ID Nr. 7)
5'-TCCTTCTCTTACAGCAATCCGAGCATCT-3' npt_H3_fw:
                                       (SEQ ID Nr. 8)
5'-GCTGTAAGAGAAGGAGTTCTATCATGATCGAG-3' npt_H4_rv:
                                       (SEQ ID Nr. 9)
5'-GCAGCCTAGGTTAATTTATCAGGCGTACGCGATCG-3'
```

The following parameters were used for the PCR for the amplification of the $P_{lacuv5}$ and the gene npt: 1×: initial denaturation, 98° C., 0:30 min; 35×: denaturation, 98° C., 0:10 min, annealing, 55° C., 0:20 min; elongation, 72° C., 0:15 min; 1×: terminal elongation, 72° C., 10 min. For the amplification of the gene MSMEG_2956, the following parameters were used: 1×: initial denaturation, 98° C., 0:30 min; 35×: denaturation, 98° C., 0:10 min, annealing, 65° C., 0:20 min; elongation, 72° C., 1 min; 1×: terminal elongation, 72° C., 10 min. For the amplification, the Phusion™ High-Fidelity Master Mix from New England Biolabs (Frankfurt) was used according to the recommendations from the manufacturer. In each case, 50 µl of the PCR reactions were then resolved on a 1% strength TAE agarose gel. The PCR, the agarose gel electrophoresis, ethidium bromide staining of the DNA and determination of the PCR fragment sizes were performed in the manner known to the person skilled in the art. In all cases, PCR fragments of the expected size could be amplified. These were 325 base pairs for $P_{lacuv5}$, 5, 3.5 kilobase pairs for MSMEG_2956 and 718 base pairs for npt. To isolate the DNA from the agarose gel, the target DNA was cut out of the gel using a scalpel and purified using the QiaQuick Gel extraction Kit in accordance with the manufacturer's instructions (Qiagen, Hilden). The purified PCR products were cloned into an EcoNI- and PacI-cut pACYCDuet-1 vector (Merck, Darmstadt) by means of recombination using the Geneart® Seamless Cloning and Assembly Kit in accordance with the manufacturer's instructions (Life Technologies, Carlsbad, Calif., USA). Chemically competent E. coli DH10β (New England Biolabs, Frankfurt) were transformed in the manner known to the person skilled in the art. The correct insertion of the target genes was checked by restriction analysis and the authenticity of the inserted genes confirmed by DNA sequencing. The finished expression vector was referred to as pACYC{Placuv5}[carA_Ms-npt-_Noc] (SEQ ID No. 10).

EXAMPLE 2

Producing an Expression Vector for the Coexpression of the Genes ald from Bacillus subtilis and Cv2025 from Chromobacterium violaceum To produce an E. coli expression vector for the genes ald (SEQ ID No. 11) from Bacillus subtilis encoding an alanine dehydrogenase (NP_391071.1) and Cv_2025 (SEQ ID No. 12) from Chromobacterium violaceum encoding a transaminase (NP_901695.1), the gene ald from Bacillus subtili s was, in exchange for the gene ald from Bacillus sphaericus, cloned into the E. coli expression vector pJ281_alaD_Bsp_TA_C.v.(ct) (sequence and production, cf. example 1 in WO/2013/024114 and SEQ ID No. 17 listed therein). The gene ald from Bacillus subtilis was amplified by PCR from chromosomal DNA from the strain Bacillus subtilis str. 168. In this connection, the following oligonucleotides were used:

```
alaDH_pCR22_fw:
                                       (SEQ ID No. 13)
5'-ATGATCATAGGGGTTCCTAAAGAG-3' alaDH_pCR22_rev:
                                       (SEQ ID No. 14)
5'-TTAAGCACCCGCCACAGATG-3'
```

The following parameters were used for the PCR: 1×: initial denaturation, 98° C., 0:30 min; 35×: denaturation, 98° C., 0:10 min, annealing, 65° C., 0:30 min; elongation, 72° C., 0:20 min; 1×: terminal elongation, 72° C., 10 min. For the amplification, the Phusion™ High-Fidelity Master Mix from New England Biolabs (Frankfurt) was used according to the recommendations from the manufacturer. In each case, 50 µl of the PCR reactions were then resolved on a 1% strength TAE agarose gel. The PCR, the agarose gel electrophoresis, ethidium bromide staining of the DNA and determination of the PCR fragment sizes were performed in the manner known to the person skilled in the art. The PCR fragment showed the expected size of 1137 base pairs and was purified from the PCR volume using the Quick PCR Purification Kit from Qiagen (Hilden) in accordance with the information from the manufacturer. For the ligation of the PCR product to the vector, 5'-phosphates were attached to the PCR product using the polynucleotide kinase (New England Biolabs, Frankfurt). In this connection, the recommendation from the manufacturer was followed.

The vector was digested with the restriction endonucleases HindIII and NdeI, and as a result, the gene present, Bacillus sphaericus ald, was removed. The restriction digest volume was resolved on a 1% strength TAE agarose gel. It was possible to identify two bands of sizes 5696 bp and 1124 bp. To isolate the vector DNA from the agarose gel, the DNA band of 5696 bp was isolated from the gel using a scalpel and purified using the Quick Gel Extraction Kit from Qiagen (Hilden) in accordance with the information from the manufacturer. To generate blunt ends, the 5'-overhangs of the purified vector DNA were filled using the Klenow fragment of DNA polymerase I (New England Biolabs, Frankfurt). In this connection, the information from the manufacturer was followed. The DNA fragment Bacillus subtilis ald with 5'-phosphate residues was ligated into the vector having blunt ends. The finished E. coli expression vector was referred to as pJ281_alaDH_B.s._TA_C.v.(Ct) (SEQ ID No. 15).

EXAMPLE 3

Producing an E. coli strain Overexpressing the Genes MSMEG_2956 from Mycobacterium smegmatis and npt from Nocardia sp., ald from Bacillus subtilis and Cv2025 from Chromobacterium violaceum To generate an E. coli strain coexpressing the genes MSMEG_2956 from Mycobacterium smegmatis encoding a fatty acid reductase (YP_887275.1) and npt from Nocardia sp. encoding a phosphopantetheinyl transferase (ABI83656.1) which phosphopantetheinylates the fatty acid reductase, in combination with the genes ald from Bacillus subtilis encoding an alanine dehydrogenase (NP_391071.1) and Cv2025 from Chromobacterium violaceum encoding a transaminase (NP_901695.1), the strain E. coli W3110 was transformed with the plasmids pACYC{Placuv5}[carA_Ms-npt_Noc] (SEQ ID No. 10) and pJ281_alaDH_B.s._TA_C.v.(ct) (SEQ ID No. 15) by means of electroporation and plated out on LB agar plates containing chloramphenicol (50 µg/ml) and kanamycin (50 µg/ml). Transformants were checked as regards the presence of the correct plasmids by plasmid preparation and analytical restriction analysis. The strain generated was referred to as E. coli W3110 pACYC{Placuv5}[carA_Ms-npt_Noc]/pJ281_alaDH_B.s._TA_C.v.(ct). The strain was used to investigate its capability for the production of dodecanediamine proceeding from dodecanedioic acid and dodecylamine proceeding from dodecanoic acid. The gene product CarA, a fatty acid reductase which is activated by the overexpressed phosphopantetheinyl transferase npt, converts the substrate dodecanoic acid or dodecanedioic acid to the respective aldehyde or dialdehyde. The function of the gene product Cv_2505 is that of converting the (di)aldehyde terminally to the dodecylamine or dodecanediamine. The alanine amino donor required for the amination reaction is provided from pyruvate by the gene product ald.

EXAMPLE 4

Production of Dodecanediamine and Dodecylamine by E. coli Strains Containing an Expression Vector for the Genes MSMEG_2956 from Mycobacterium smegmatis and npt from Nocardia sp. in Combination with an Expression Vector for the Genes ald from Bacillus subtilis and Cv_2025 from Chromobacterium violaceum The strain generated in example 3 was used to investigate its capability in relation to the production of dodecylamine and dodecanediamine. The biotransformation of dodecanoic acid and dodecanedioic acid to dodecylamine and dodecanediamine, respectively, was carried out in the 8-fold parallel fermentation system from DASGIP. The procedure for this was as follows: For the fermentation, 1 L reactors were used. The pH probes were calibrated by means of a two-point calibration with measurement solutions of pH 4.0 and pH 7.0. The reactors were filled with 300 mL of drinking water and autoclaved for 20 min at 121° C. in order to ensure sterility. Then, the pO2 probes were polarized on the DASGIP system overnight (for at least 6 h). The next morning, the water was removed under the clean bench and replaced with 300 mL of high-cell-density medium containing 50 mg/L chloramphenicol and 50 mg/L kanamycin. Subsequently, the pO2 probes were calibrated using a single-point calibration (stirrer: 400 rpm/aeration: 10 sL/h air) and the feed, correcting agent and induction agent paths were cleaned by means of clean-in-place. To this end, the hoses were flushed with 70% ethanol, then with 1 M NaOH, then with sterile demineralized water and finally filled with the particular media.

The E. coli strain producing dodecanediamine and dodecylamine was firstly cultured from the cryogenic culture in LB medium (25 mL in a 100 mL baffled flask) containing the aforementioned antibiotics overnight at 37° C. and 200 rpm, for about 18 h. Then, 2 mL of the culture were inoculated into high-cell-density medium (15 g/L glucose (30 mL/L of a separately autoclaved 500 g/L stock solution containing 1% $MgSO_4 \cdot 7H_2O$ and 2.2% $NH_4Cl$), 1.76 g/L $(NH_4)_2SO4$, 19.08 g/L $K_2HPO_4$, 12.5 g/L $KH_2PO_4$, 6.66 g/L yeast extract, 2.24 g/L trisodium citrate dihydrate, ammonium ferric citrate solution, 17 mUL of a separately autoclaved 1% strength stock solution, trace element solution, 5 mUL separately autoclaved stock solution (36.50 g/L HCl (37%), 1.91 g/L $MnCl_2 \cdot 4H_2O$, 1.87 g/L $ZnSO_4 \cdot 7H_2O$, 0.84 g/L ethylenediaminetetraacetic acid dihydrate, 0.30 g/L $H_3BO_3$, 0.25 g/L $Na_2MoO_4 \cdot 2H_2O$, 4.70 g/L $CaCl_2 \cdot 2H_2O$, 17.80 g/L $FeSO_4 \cdot 7H_2O$, 0.15 g/L $CuCl_2 \cdot 2H_2O$)) (25 mL in a 100 mL baffled flask) containing the aforementioned antibiotics and incubated at 37° C./200 rpm for a further 5.5 h. The reactors were inoculated at an optical density of 0.1 by an appropriate volume of the pre-culture being filled into a 5 mL syringe (under sterile conditions) and the reactors being inoculated by means of a needle across a septum covered with 70% ethanol.

The following standard program was used:

| DO regulator | | pH regulator | |
|---|---|---|---|
| Preset | 0% | Preset | 0 ml/h |
| P | 0.1 | P | 5 |
| Ti | 300 s | Ti | 200 s |
| Min | 0% | Min | 0 mlL/h |
| Max | 100% | Max | 40 mL/h |

| N (rotation) | from | to | XO2 (gas mixture) | from | to | F (gas flow rate) | from | to |
|---|---|---|---|---|---|---|---|---|
| Growth and biotransformation | 0% 400 rpm | 30% 1500 rpm | Growth and biotransformation | 0% 21% | 100% 21% | Growth and biotransformation | 15% 6 sL/h | 80% 72 sL/h |

| Script | |
|---|---|
| Trigger activated | 31% DO (1/60 h) |
| IPTG induction | 2 h after feed start |
| Feed trigger | 50% DO |
| Feed rate | 3 [mL/h] |

The experiment carried out can be divided into two phases: growth, during which the cells are to reach a certain optical density, and subsequent biotransformation, in which, after addition of the substrates dodecanoic acid, oleic acid and dodecanedioic acid, a conversion to dodecylamine, oleylamine and dodecanediamine, respectively, is to take place by enzymes formed during expression. The pH levels were unilaterally adjusted to pH 6.8 using ammonia (12.5%). During growth and biotransformation, the dissolved oxygen (DO) in the culture was adjusted at 30% by means of stirrer speed and aeration rate. The fermentation was carried out as a fed batch, with the feed start, 5 g/Lh glucose feed (500 g/L glucose containing 1% $MgSO_4*7H_2O$ and 2.2% $NH_4Cl$), being triggered via a DO peak. With the feed start, the temperature was also lowered from previously 37° C. to 30° C. The expression of the transaminase, alanine dehydrogenase, carboxylic acid reductase and phosphopantetheinyl transferase was induced 2 h after the feed start by the automated addition of 1 mM IPTG. Before the start of biotransformation, the optical density of the culture broths was determined.

The start of the biotransformation phase took place 1 h or 12 h after the feed start. To this end, 150 mL or 75 mL of a mixture of dodecanoic acid or dodecanedioic acid and oleic acid (technical-grade 90%) were added as a batch to the fermentation broth. To provide an amino group donor for the transaminase, 5 mL of a 3 M ammonium sulphate solution were added to the fermentation broth 30 minutes before the biotransformation start. For sampling, 2 mL of fermentation broth were removed from the tank and a portion thereof was diluted 1/20 in a and in a mixture of 80% acetonitrile, 20% water and 0.1% formic acid and extracted. Samples were taken from all reactors at 1.25 h, 2.75 h, 4.25 h, 18.25 h, and 21.75 h after the start of biotransformation. The conversion rates for oxygen (OTR=oxygen transfer rate) and carbon (CTR=carbon transfer rate) were determined during the fermentation via the waste-gas analyses on the DASGIP systems. The fermentation was ended 21.75 h after the start of biotransformation. The stirrer, the aeration system, the temperature control and pH control were turned off and the tanks were left to stand undisturbed for 5-10 minutes.

HPLC-ESI/MS Scan Method

The samples were qualitatively assessed by means of HPLC/MS coupling with high-resolution MS detection in the scan mode.

The following instruments were used here:
Accela HPLC system (Thermo Scientific, Waltham, Mass., USA) with autosampler, quaternary pump, PDA detector and column oven
LTQ-FT mass spectrometer (Thermo Scientific, Waltham, Mass., USA) with ESI source
HPLC column: Kinetex C18, 100×2.1 mm, particle size: 2.6 µm, pore size 100 Å (Phenomenex; Aschaffenburg)

The samples were prepared by pipetting 1950 µl of solvent (80% (v/v) acetonitrile, 20% double-distilled $H_2O$ (v/v), +0.1% formic acid) and 50 µl of sample into a 2 ml reaction vessel. The mixture was vortexed for about 10 seconds and then centrifuged at about 13 000 rpm for 5 min. The clear supernatant was removed using a pipette.

The HPLC separation was carried out with the aforementioned HPLC column. The injection volume was 0.5 µL, the column temperature 40° C., and the flow rate 0.3 mL/min. The mobile phase was composed of eluent A (0.02% strength (v/v) aqueous trifluoroacetic acid) and eluent B (acetonitrile with 0.015% (v/v) trifluoroacetic acid). The following gradient profile was used:

| Time [min] | Eluent A [%] | Eluent B [%] |
|---|---|---|
| 0 | 98 | 2 |
| 2 | 98 | 2 |
| 17 | 2 | 98 |
| 32 | 2 | 98 |

The ESI-MS analysis was carried out in the positive mode with the following parameters of the ESI source:

| ESI voltage: | 4 kV |
|---|---|
| Capillary temperature | 300° C. |
| Sheath gas flow | 40 |
| Aux gas flow | 5 |
| Sweep gas flow | 3 |

The detection was carried out within a mass range of m/z=100 to 1000. The mass spectrometry resolution was R=100 000.

The results are shown in the table below.

| | | MS intensity [−] | | |
|---|---|---|---|---|
| Substrate | Induction | Dodecanediamine | Dodecylamine | Oleylamine |
| LA/oleic acid (150 ml) | 1 mM IPTG (12 h) | n.d. | 1,160,000 | 23,700 |
| DDA/oleic acid (75 ml) | 1 mM IPTG in $H_2O$/ethanol (12 h) | 742,000 | n.d. | 18,000 |
| DDA/oleic acid (150 ml) | 1 mM IPTG (1 h) | 30,700 | n.d. | n.d. |
| DDA/oleic acid (150 ml) | 1 mM IPTG (12 h) | 23,500 | n.d. | n.d. |

Qualitative detection of monoamines and diamines in the fermentation broth of the strain E. coli W3110 pACYC{Placuv5}[carA_Ms-npt_Noc]/pJ281_alaDH_B.s._TA_C.v.(ct) after a 21.75 h process time
(n.d. = not detectable,
LA = lauric acid,
DDA = dodecanedioic acid).

Further data are illustrated in FIG. 1.

1,12-dodecanediamine and dodecylamine are quantitatively determined by means of HPLC/UV measurement, after derivatization by means of ortho-phthaldialdehyde. The methanolic supernatant was measured. The most important chromatographic parameters are summarized in the following table.

| | |
|---|---|
| Column | Luna 5u C8, 100 Å, 150 × 4.60 mm (Phenomenex; Aschaffenburg) |
| HPLC system | Agilent 1200 |
| Eluent A | 2.5 mL of acetic acid (100%) to 1 L of double-distilled water, pH adjustment with sodium hydroxide solution to pH 6.0 |
| Eluent B | methanol |
| Column temp. | 40° C. |
| Flow rate | 1 mL/min |
| Gradient | 0.0-1 min: 30.0% B, 1.0-17.0 min: 90.0% B, 17-19.5 min: 90.0% B, 19.6-20.5 min: 30.0% B |
| Detector | DAD, 334 nm |
| Derivatization/ injection volume | Automatic derivatization by means of injector program, 1 μL of sample is reacted with 9 μL of derivatization reagent; composition of derivatization reagent: 10 g/L o-phthaldialdehyde dissolved in borate buffer (0.4 mol/L), with addition of mercaptoethanol (5 mL/L) and methanol (100 mL/L) |
| Calibration | External calibration, measurement range 50-1000 mg/L, 5-point calibration, calibration before and after the sample series, averaging via both calibration series, quadratic regression |

The results are shown in the tables which follow.

| Substrate | Induction | Dodecylamine [mg/L] | Dodecanediamine [mg/L] |
|---|---|---|---|
| DDA/oleic acid (75 ml) | 1 mM IPTG in H₂O/ethanol (12 h) | n.d. | 40.5 |
| DDA/oleic acid (150 mL) | 1 mM IPTG (1 h) | n.d. | 3.1 |
| DDA/oleic acid (150 ml) | 1 mM IPTG (12 h) | n.d. | <1*⁾ |
| LA/oleic acid (150 ml) | 1 mM IPTG (12 h) | 11.6 | n.d. |

Quantification of monoamines and diamines in the fermentation broth of the strain *E. coli* W3110 pACYC{Placuv5}[carA_Ms-npt_Noc]/pJ281_alaDH_B.s._TA_C.v.(ct) after a 21.75 h process time
(n.d. = not detectable,
*⁾lower than the detection limit,
DDA = dodecanedioic acid,
LA = lauric acid).

It was shown that the strains are capable of producing, from dodecanoic acid, dodecanedioic acid and oleic acid, the respective amines dodecylamine, dodecanediamine and oleylamine.

EXAMPLE 5

Producing an Expression Vector for the Expression of the Gene αDOX Encoding an α-dioxygenase from *Oryza sativa*

To produce a vector for the expression of αDOX (Os12g0448900, SEQ ID No. 16) from *Oryza sativa* encoding an α-dioxygenase (NP_001066718.1), the gene was codon-optimized for expression in *Escherichia coli*, synthesized and, at the same time, an upstream NdeI restriction site and a downstream AvrII restriction site were introduced. The synthesized DNA fragment was digested with the restriction endonucleases NdeI and AvrII and ligated into the correspondingly cut vector pACYC{Placuv5}[carA_Ms-npt_Noc] (SEQ ID No. 10) with removal of the genes carA_Ms and npt_Noc. The lacuv5 promoter (SEQ ID No. 3) present in the vector was retained. The finished vector was referred to as pACYC{Placuv5}[DOX_Os(co_Ec)] (SEQ ID No. 17). The vector pACYC is an *E. coli* vector which mediates chloramphenicol resistance and also bears a p15A origin of replication and thus has a low copy number (10-15 copies per cell).

EXAMPLE 6

Producing an *E. coli* Strain having a Deletion in the Gene bioH, Overexpressing the Genes αDOX from *Oryza sativa*, ald from *Bacillus subtilis* and Cv2025 from *Chromobacterium violaceum*

To generate an *E. coli* strain which coexpresses the gene αDOX from *Oryza sativa* encoding an α-dioxygenase (NP_001066718.1) in combination with the genes ald (SEQ ID No. 11) from *Bacillus subtilis* encoding an alanine dehydrogenase (NP_391071.1) and Cv2025 (SEQ ID No. 12) from *Chromobacterium violaceum* encoding a transaminase (NP_901695.1), the strain *E. coli* W3110 ΔbioH (production: see EP12007663, example 1) was transformed with the plasmids pACYC{Placuv5}[DOX_Os(co_Ec)] (SEQ ID No. 17) and pJ281_alaDH_B.s._TA_C.v.(ct) (SEQ ID No. 15) by means of electroporation and plated out on LB agar plates containing chloramphenicol (50 μg/ml) and kanamycin (50 μg/ml). Transformants were checked as regards the presence of the correct plasmids by plasmid preparation and analytical restriction analysis. The strain generated was referred to as *E. coli* ΔbioH pACYC{Placuv5}[DOX_Os (co_Ec)]/pJ281_alaDH_B.s._TA_C.v.(ct).

The strain was used to investigate its capability for the production of methyl aminoundecanoate proceeding from methyl dodecanedioate.

EXAMPLE 7

Production of Methyl Aminoundecanoate Proceeding from Methyl Dodecanedioate by an *E. coli* Strain Containing an Expression Vector for the Gene αDOX from *Oryza sativa* in Combination with an Expression Vector for the Genes ald from *Bacillus subtilis* and Cv_2025 from *Chromobacterium violaceum*

The strain described in example 8 was used to investigate its capability in relation to the production of methyl aminoundecanoate. The procedure for this was as follows:

The strain under investigation was firstly spread out on an LB agar plate containing 50 μg/ml chloramphenicol and 50 μg/ml kanamycin and incubated overnight at 37° C. As control, the strain *E. coli* W3110 αbioH was additionally spread out on an LB agar plate not containing antibiotics. The strains were then cultured in Luria-Bertani broth, Miller (Merck, Darmstadt) containing 50 µg/ml chloramphenicol and 50 µg/ml kanamycin (for the plasmid-bearing strain) as a 20 ml pre-culture from a single colony in each case. As main culture, 100 ml of LB broth containing 50 µg/ml chloramphenicol and 50 µg/ml kanamycin were initially charged into a 500 ml Erlenmeyer flask containing baffles and inoculated with 2 ml from the pre-culture. Culturing was firstly carried out at 37° C. and 200 rpm in an incubator shaker. Upon attainment of an optical density (600 nm) of 0.5-0.7, the gene expression was induced by addition of 1 mM IPTG. Further culturing was carried out overnight at 22° C. and 200 rpm. The following day, the cultures were harvested by a 10-minute centrifugation at 4° C. and 5525× g. The supernatant was discarded and the cell pellet washed in 200 mM potassium phosphate buffer (pH 7.5). The cell pellet was lastly taken up in 200 mM potassium phosphate buffer containing 50 mM ammonium chloride and 0.5% (w/v) glucose, and so an OD (600 nm) of 20 was attained. 12.5 mM methyl dodecanedioate (abcr, Karlsruhe) in ethanol were added to the cell suspension and gently shaken for 4 hours at 30° C. and 300 rpm. During the incubation, samples were taken at the times 0 min, 60 min, 120 min, 180 min and 240 min and extracted in a mixture of 80% acetonitrile, 20% water and 0.1% formic acid. The supernatant was analysed by means of HPLC/MS analysis. The results are shown in the table below.

| Strain | Time [min] | Peak area Methyl aminoundecanoate |
|---|---|---|
| E. coli W3110 ΔbioH | 0 | n.d. |
| | 120 | n.d. |
| | 180 | n.d. |
| | 240 | n.d. |
| E. coli W3110 ΔbioH pACYC{Placuv5}[DOX]/ pJ281_alaDH_B.s._TA_C.v.(ct) | 0 | n.d. |
| | 120 | 57616 |
| | 180 | 371989 |
| | 240 | 1764605 |

Production of methyl aminoundecanoate with E. coli W3110 ΔbioH overexpressing αDOX from Oryza sativa, ald from Bacillus subtilis and Cv_2025 from Chromobacterium violaceum. Peak areas are specified (n.d. = not detectable).

It was possible to show that the strain E. coli W3110 ΔbioH pACYC{Placuv5}[DOX]/pJ281_alaDH_B.s._TA_C.v.(ct) is capable of forming methyl aminoundecanoate proceeding from methyl dodecanedioate.

The invention claimed is:

1. A whole-cell catalyst, comprising heterologous expression of: a combination of a recombinant fatty acid reductase and a phosphopantetheinyl transferase capable of phosphopantetheinylating the fatty acid reductase; and a transaminase, wherein the recombinant fatty acid reductase and the phosphopantetheinyl transferase, and the transaminase, are expressed in the whole-cell catalyst, and wherein the whole-cell catalyst is a microorganism.

2. The whole-cell catalyst according to claim 1, further comprising:
an amino acid dehydrogenase expressed in the whole-cell catalyst.

3. The whole-cell catalyst according to claim 1, further comprising:
an alkane hydroxylase expressed in the whole-cell catalyst.

4. The whole-cell catalyst according to claim 1, further comprising:
a polypeptide of the AlkL family expressed in the whole-cell catalyst.

5. The whole-cell catalyst according to claim 1, further comprising:
an alcohol dehydrogenase expressed in the whole-cell catalyst.

6. The whole-cell catalyst according to claim 1, wherein an activity of at least one enzyme involved in β-oxidation is reduced as compared to an activity of the at least one enzyme in the wild type of the whole-cell catalyst.

7. The whole-cell catalyst according to claim 1, wherein an activity of BioH is reduced or elevated as compared to an activity of BioH in the wild type of the whole-cell catalyst.

8. The whole-cell catalyst according to claim 1, wherein an activity of FadL is elevated as compared to an activity of FadL in the wild type of the whole-cell catalyst.

9. A reaction mixture, comprising:
the whole-cell catalyst according to claim 1 in an aqueous solution; and
a carboxylic acid, a dicarboxylic acid, or a monoester thereof having the formula (I):

$$R^1\text{-A-COOR}^2 \qquad (I),$$

wherein $R^1$ is —H or $COOR^3$,
$R^2$ and $R^3$ are each independently selected from the group consisting of H, methyl, ethyl and propyl, with the proviso that at least one of the radicals $R^2$ and $R^3$ is H, and
A is an unbranched, branched, linear, cyclic, substituted or unsubstituted hydrocarbon group having at least four carbons.

10. The whole-cell catalyst according to claim 1, wherein at least one of the phosphopantetheinyl transferase and the transaminase is recombinant.

11. The whole-cell catalyst according to claim 1, further comprising:
at least one of a recombinant amino acid dehydrogenase, a recombinant alkane hydroxylase, a recombinant polypeptide of the AlkL family, and a recombinant alcohol dehydrogenase, expressed in the whole-cell catalyst.

12. The whole-cell catalyst according to claim 1, wherein the recombinant fatty acid reductase is encoded by a gene having at least 70% sequence identity to the nucleotide sequence of SEQ ID NO: 1, the phosphopantetheinyl transferase is encoded by a gene having at least 70% sequence identity to the nucleotide sequence of SEQ ID NO: 2, and the transaminase is encoded by a gene having at least 70% sequence identity to the nucleotide sequence of SEQ ID NO: 12.

13. The whole-cell catalyst according to claim 1, further comprising: an alanine dehydrogenase expressed in the whole-cell catalyst and having at least 95% sequence identity to the nucleotide sequence of SEQ ID NO: 11, wherein the recombinant fatty acid reductase is encoded by a gene having at least 95% sequence identity to the nucleotide sequence of SEQ ID NO: 1, the phosphopantetheinyl transferase is encoded by a gene having at least 95% sequence identity to the nucleotide sequence of SEQ ID NO: 2, and the transaminase is encoded by a gene having at least 95% sequence identity to the nucleotide sequence of SEQ ID NO: 12.

\* \* \* \* \*

SEQUENCE LISTING

<160> NUMBER OF SEQ ID NOS: 17

<210> SEQ ID NO 1
<211> LENGTH: 3507
<212> TYPE: DNA
<213> ORGANISM: Mycobacterium smegmatis

<400> SEQUENCE: 1

```
atgacgatcg aaacgcgcga agaccgcttc aaccggcgca ttgaccactt gttcgaaacc      60
gacccgcagt tcgccgccgc ccgtcccgac gaggcgatca gcgcggctgc cgccgatccg     120
gagttgcgcc ttcctgccgc ggtcaaacag attctggccg gctatgcgga ccgccctgcg     180
ctcggcaagc gcgccgtcga gttcgtcacc gacgaagaag gccgcaccac cgcgaagctc     240
ctgccccgct tcgacaccat cacctaccgt cagctcgcag gccggatcca ggccgtgacc     300
aatgcctggc acaaccatcc ggtgaatgcc ggtgaccgcg tggccatcct gggtttcacc     360
agtgtcgact acacgacgat cgacatcgcc ctgctcgaac tcggcgccgt gtccgtaccg     420
ctgcagacca gtgcgccggt ggcccaactg cagccgatcg tcgccgagac cgagcccaag     480
gtgatcgcgt cgagcgtcga cttcctcgcc gacgcagtcg ctctcgtcga gtccgggccc     540
gcgccgtcgc gactggtggt gttcgactac agccacgagg tcgacgatca gcgtgaggcg     600
ttcgaggcgg ccaagggcaa gctcgcaggc accggcgtcg tcgtcgagac gatcaccgac     660
gtactggacc gcgggcggtc actcgccgac gcaccgctct acgtgcccga cgagaccgac     720
ccgctgaccc ttctcatcta cacctccggc agcaccggca ctcccaaggg cgcgatgtac     780
cccgagtcca agaccgccac gatgtggcag gccgggtcca aggccggtg ggacgagacc     840 ctcggcgtga tgccgtcaat caccctgaac ttcatgccca tgagtcacgt catgggcgc      900 ggcatcctgt gcagcacact cgccagcggc ggaaccgcgt acttcgccgc acgcagcgac     960
ctgtccacct tcctggagga cctcgccctc gtgcggccca cgcagctcaa cttcgttcct    1020
cgcatctggg acatgctgtt ccaggagtac cagagccgcc tcgacaaccg ccgcgccgag    1080
ggatccgagg accgagccga agccgcagtc ctcgaagagg tccgcaccca actgctcggc    1140
```

```
gggcgattcg tttcggccct gaccggatcg gctcccatct cggcggagat gaagagctgg    1200
gtcgaggacc tgctcgacat gcatctgctg gagggctacg gctccaccga ggccggcgcg    1260
gtgttcatcg acgggcagat ccagcgcccg ccggtcatcg actacaagct ggtcgacgtg    1320
cccgatctcg gctacttcgc cacggaccgg ccctacccgc gcggcgaact tctggtcaag    1380
tccgagcaga tgttccccgg ctactacaag cgtccggaga tcaccgccga gatgttcgac    1440
gaggacgggt actaccgcac cggcgacatc gtcgccgagc tcgggcccga ccatctcgaa    1500
tacctcgacc gccgcaacaa cgtgctgaaa ctgtcgcagg gcgaattcgt cacggtctcc    1560
aagctggagg cggtgttcgg cgacagcccc ctggtacgcc agatctacgt ctacggcaac    1620
agcgcgcggt cctatctgct ggcggtcgtg gtcccgaccg aagaggcact gtcacgttgg    1680
gacggtgacg aactcaagtc gcgcatcagc gactcactgc aggacgcggc acgagccgcc    1740
ggattgcagt cgtatgagat cccgcgtgac ttcctcgtcg agacaacacc tttcacgctg    1800
gagaacggcc tgctgaccgg tatccgcaag ctggcccggc cgaaactgaa ggcgcactac    1860
ggcgaacgcc tcgaacagct ctacaccgac ctggccgagg ggcaggccaa cgagttgcgc    1920
gagttgcgcc gcaacggagc cgaccggccc gtgtcgaga ccgtcagccg cgccgcggtc    1980
gcactgctcg gtgcctccgt cacggatctg cggtccgatg cgcacttcac cgatctgggt    2040
ggagattcgt tgtcggcctt gagcttctcg aacctgttgc acgagatctt cgatgtcgac    2100
gtgccggtcg gcgtcatcgt cagcccggcc accgacctgg caggcgtcgc ggcctacatc    2160
gagggcgaac tgcgcggctc caagcgcccc acatacgcgt cggtgcacgg gcgcgacgcc    2220
accgaggtgc gcgcgcgtga tctcgccctg ggcaagttca tcgacgccaa gaccctgtcc    2280
gccgcgccgg gtctgccgcg ttcgggcacc gagatccgca ccgtgctgct gaccggcgcc    2340
accgggttcc tgggccgcta tctggcgctg gaatggctgg agcgcatgga cctggtggac    2400
ggcaaggtga tctgcctggt gcgcgcccgc agcgacgacg aggcccgggc gcgtctggac    2460
gccacgttcg acaccgggga cgcgacactg ctcgagcact accgcgcgct ggcagccgat    2520
cacctcgagg tgatcgccgg tgacaagggc gaggccgatc tgggtctcga ccacgacacg    2580
tggcagcgac tggccgacac cgtcgatctg atcgtcgatc cggccgccct ggtcaatcac    2640
gtcctgccgt acagccagat gttcggaccc aatgcgctcg gcaccgccga actcatccgg    2700
atcgcgctga ccaccacgat caagccgtac gtgtacgtct cgacgatcgg tgtgggacag    2760
ggcatctccc ccgaggcgtt cgtcgaggac gccgacatcc gcgagatcag cgcgacgcgc    2820
cgggtcgacg actcgtacgc caacggctac ggcaacagca gtgggccgg cgaggtcctg    2880 ctgcgggagg cgcacgactg gtgtggtctg ccggtctcgg tgttccgctg cgacatgatc    2940
ctggccgaca cgacctactc gggtcagctg aacctgccgg acatgttcac ccgcctgatg    3000
ctgagcctcg tggcgaccgg catcgcgccc ggttcgttct acgaactcga tgcggacggc    3060
aaccggcagc gcgcccacta cgacgggctg ccgtgagt tcatcgccga ggcgatctcc    3120
accatcggct cgcaggtcac cgacggattc gagacgttcc acgtgatgaa cccgtacgac    3180
gacggcatcg gcctcgacga gtacgtggac tggctgatcg aggccggcta ccccgtgcac    3240
cgcgtcgacg actacgccac ctggctgagc cggttcgaaa ccgcactgcg ggccctgccg    3300
gaacggcaac gtcaggcctc gctgctgccg ctgctgcaca actatcagca gccctcaccg    3360
cccgtgtgcg gtgccatggc acccaccgac cggttccgtg ccgcggtgca ggacgcgaag    3420
atcggccccg acaaggacat tccgcacgtc acggccgacg tgatcgtcaa gtacatcagc    3480
```

```
aacctgcaga tgctcggatt gctgtaa                                         3507

<210> SEQ ID NO 2
<211> LENGTH: 672
<212> TYPE: DNA
<213> ORGANISM: Nocardia sp.

<400> SEQUENCE: 2
atgatcgaga caattttgcc tgctggtgtc gagtcggctg agctgctgga gtatccggag      60
gacctgaagg cgcatccggc ggaggagcat ctcatcgcga agtcggtgga gaagcggcgc     120
cgggacttca tcggggccag gcattgtgcc cggctggcgc tggctgagct cggcgagccg     180
ccggtggcga tcggcaaagg ggagcggggt gcgccgatct ggccgcgcgg cgtcgtcggc     240
agcctcaccc attgcgacgg atatcgggcc gcggcgtgg cgcacaagat gcgcttccgt      300
tcgatcggca tcgatgccga ccgcacgcg acgctgcccg aaggcgtgct ggattcggtc      360
agcctgccgc cggagcggga gtggttgaag accaccgatt ccgcactgca cctggaccgt     420
ttactgttct gcgccaagga agccacctac aaggcgtggt ggccgctgac cgcgcgctgg     480
ctcggcttcg aggaagcgca catcaccttc gagatcgaag acggctccgc cgattccggc     540
aacggcacct ttcacagcga gctgctggtg ccggacagcc gaatgacgg tgggacgccg      600 ctgctttcgt tcgacggccg gtggctgatc gccgacgggt tcatcctcac cgcgatcgcg     660
tacgcctgat aa                                                         672

<210> SEQ ID NO 3
<211> LENGTH: 153
<212> TYPE: DNA
<213> ORGANISM: Artificial Sequence
<220> FEATURE:
<223> OTHER INFORMATION: promotor

<400> SEQUENCE: 3
ggcagtgagc gcaacgcaat taatgtaagt tagctcactc attaggcacc ccaggcttga      60
cactttatgc ttccggctcg tataatgtgt ggaattgtga gcggataaca ataacaattt     120
cacacaggat ctaggaacca aggagagtgg cat                                  153

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
ttatgcgact cctgctggct atggtgggat ttcc                                  34

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gatcgtcata tgccactctc cttggttcc                                        29

<210> SEQ ID NO 6
<211> LENGTH: 25
<212> TYPE: DNA
<213> ORGANISM: Artificial Sequence
```

<220> FEATURE:
<223> OTHER INFORMATION: Primer

<400> SEQUENCE: 6
tggcatatga cgatcgaaac gcgcg    25

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
tccttctctt acagcaatcc gagcatct    28

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
gctgtaagag aaggagttct atcatgatcg ag    32

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
gcagcctagg ttaatttatc aggcgtacgc gatcg    35

<210> SEQ ID NO 10
<211> LENGTH: 8047
<212> TYPE: DNA
<213> ORGANISM: Artificial Sequence
<220> FEATURE:
<223> OTHER INFORMATION: Vector

<400> SEQUENCE: 10
attaacctag gctgctgcca ccgctgagca ataactagca taaccccttg gggcctctaa     60
acgggtcttg aggggttttt tgctgaaacc tcaggcattt gagaagcaca cggtcacact    120
gcttccggta gtcaataaac cggtaaacca gcaatagaca taagcggcta tttaacgacc    180
ctgccctgaa ccgacgaccg ggtcgaattt gctttcgaat ttctgccatt catccgctta    240
ttatcactta ttcaggcgta gcaccaggcg tttaagggca ccaataactg ccttaaaaaa    300
attacgcccc gccctgccac tcatcgcagt actgttgtaa ttcattaagc attctgccga    360
catggaagcc atcacagacg gcatgatgaa cctgaatcgc cagcggcatc agcaccttgt    420
cgccttgcgt ataatatttg cccatagtga aaacggggggc gaagaagttg tccatattgg    480
ccacgtttaa atcaaaactg gtgaaactca cccagggatt ggctgagacg aaaaacatat    540
tctcaataaa ccctttaggg aaataggcca ggttttcacc gtaacacgcc acatcttgcg    600
aatatatgtg tagaaactgc cggaaatcgt cgtggtattc actccagagc gatgaaaacg    660
tttcagtttg ctcatggaaa acggtgtaac aagggtgaac actatcccat atcaccagct    720
caccgtcttt cattgccata cggaactccg gatgagcatt catcaggcgg gcaagaatgt    780

```
gaataaaggc cggataaaac ttgtgcttat ttttctttac ggtctttaaa aaggccgtaa    840
tatccagctg aacggtctgg ttataggtac attgagcaac tgactgaaat gcctcaaaat    900
gttctttacg atgccattgg gatatatcaa cggtggtata tccagtgatt ttttctcca    960 ttttagcttc cttagctcct gaaaatctcg ataactcaaa aaatacgccc ggtagtgatc   1020
ttatttcatt atggtgaaag ttggaacctc ttacgtgccg atcaacgtct catttttcgcc   1080 aaaagttggc ccagggcttc ccggtatcaa cagggacacc aggatttatt tattctgcga   1140
agtgatcttc cgtcacaggt atttattcgg cgcaaagtgc gtcgggtgat gctgccaact   1200
tactgattta gtgtatgatg gtgtttttga ggtgctccag tggcttctgt ttctatcagc   1260
tgtccctcct gttcagctac tgacggggtg gtgcgtaacg gcaaaagcac cgccggacat   1320
cagcgctagc ggagtgtata ctggcttact atgttggcac tgatgagggt gtcagtgaag   1380
tgcttcatgt ggcaggagaa aaaaggctgc accggtgcgt cagcagaata tgtgatacag   1440
gatatattcc gcttcctcgc tcactgactc gctacgctcg gtcgttcgac tgcggcgagc   1500
ggaaatggct tacgaacggg gcggagattt cctggaagat gccaggaaga tacttaacag   1560
ggaagtgaga gggccgcggc aaagccgttt ttccataggc tccgcccccc tgacaagcat   1620
cacgaaatct gacgctcaaa tcagtggtgg cgaaacccga caggactata agataccag   1680 gcgtttcccc tggcggctcc ctcgtgcgct ctcctgttcc tgcctttcgg tttaccggtg   1740
tcattccgct gttatggccg cgtttgtctc attccacgcc tgacactcag ttccgggtag   1800
gcagttcgct ccaagctgga ctgtatgcac gaaccccccg ttcagtccga ccgctgcgcc   1860
ttatccggta actatcgtct tgagtccaac ccggaaagac atgcaaaagc accactggca   1920
gcagccactg gtaattgatt tagaggagtt agtcttgaag tcatgcgccg gttaaggcta   1980
aactgaaagg acaagttttg gtgactgcgc tcctccaagc cagttacctc ggttcaaaga   2040
gttggtagct cagagaacct tcgaaaaacc gccctgcaag gcggtttttt cgttttcaga   2100
gcaagagatt acgcgcagac caaaacgatc tcaagaagat catcttatta atcagataaa   2160
atatttctag atttcagtgc aatttatctc ttcaaatgta gcacctgaag tcagccccat   2220
acgatataag ttgtaattct catgttagtc atgccccgcg cccaccggaa ggagctgact   2280
gggttgaagg ctctcaaggg catcggtcga gatcccggtg cctaatgagt gagctaactt   2340
acattaattg cgttgcgctc actgcccgct ttccagtcgg gaaacctgtc gtgccagctg   2400
cattaatgaa tcggccaacg cgcggggaga ggcggtttgc gtattgggcg ccagggtggt   2460
ttttcttttc accagtgaga cgggcaacag ctgattgccc ttcaccgcct ggccctgaga   2520
gagttgcagc aagcggtcca cgctggtttg ccccagcagg cgaaaatcct gtttgatggt   2580
ggttaacggc gggatataac atgagctgtc ttcggtatcg tcgtatccca ctaccgagat   2640
gtccgcacca acgcgcagcc cggactcggt aatggcgcgc attgcgccca cgccatctg   2700 atcgttggca accagcatcg cagtgggaac gatgccctca ttcagcattt gcatggtttg   2760
ttgaaaaccg gacatggcac tccagtcgcc ttcccgttcc gctatcggct gaatttgatt   2820
gcgagtgaga tatttatgcc agccagccag acgcagacgc gccgagacag aacttaatgg   2880
gcccgctaac agcgcgattt gctggtgacc caatgcgacc agatgctcca cgcccagtcg   2940
cgtaccgtct tcatgggaga aataatact gttgatgggt gtctggtcag agacatcaag   3000
aaataacgcc ggaacattag tgcaggcagc ttccacagca atggcatcct ggtcatccag   3060
cggatagtta atgatcagcc cactgacgcg ttgcgcgaga agattgtgca ccgccgcttt   3120
acaggcttcg acgccgcttc gttctaccat cgacaccacc acgctggcac ccagttgatc   3180
```

```
ggcgcgagat ttaatcgccg cgacaatttg cgacggcgcg tgcagggcca gactggaggt    3240
ggcaacgcca atcagcaacg actgtttgcc cgccagttgt tgtgccacgc ggttgggaat    3300
gtaattcagc tccgccatcg ccgcttccac ttttccccgc gttttcgcag aaacgtggct    3360
ggcctggttc accacgcggg aaacggtctg ataagagaca ccggcatact ctgcgacatc    3420
gtataacgtt actggtttca cattcaccac cctgaattga ctctcttccg ggcgctatca    3480
tgccataccg cgaaaggttt tgcgccattc gatggtgtcc gggatctcga cgctctccct    3540
tatgcgactc ctgctggcta tggtgggatt tcccttgctg aaatgggaga tccgatcatg    3600
ttcgagctct tattcaaata cactgctgtg ttggcggtaa cgttctcga gcgcggccgc    3660 gcgatcgcac ctggtgttta acggccggc ccctgcaggg gcagtgagcg caacgcaatt    3720
aatgtaagtt agctcactca ttaggcaccc caggcttgac actttatgct tccggctcgt    3780
ataatgtgtg gaattgtgag cggataacaa taacaatttc acacaggatc taggaaccaa    3840
ggagagtggc atatgacgat cgaaacgcgc gaagaccgct tcaaccggcg cattgaccac    3900
ttgttcgaaa ccgacccgca gttcgccgcc gcccgtcccg acgaggcgat cagcgcggct    3960
gccgccgatc cggagttgcg ccttcctgcc gcggtcaaac agattctggc cggctatgcg    4020
gaccgccctg cgctcggcaa gcgcgccgtc gagttcgtca ccgacgaaga aggccgcacc    4080
accgcgaagc tcctgccccg cttcgacacc atcacctacc gtcagctcgc aggccggatc    4140
caggccgtga ccaatgcctg gcacaaccat ccggtgaatg ccggtgaccg cgtggccatc    4200
ctgggtttca ccagtgtcga ctacacgacg atcgacatcg ccctgctcga actcggcgcc    4260
gtgtccgtac cgctgcagac cagtgcgccg gtggcccaac tgcagccgat cgtcgccgag    4320
accgagccca aggtgatcgc gtcgagcgtc gacttcctcg ccgacgcagt cgctctcgtc    4380
gagtccgggc ccgcgccgtc gcgactggtg tgttcgact acagccacga ggtcgacgat    4440
cagcgtgagg cgttcgaggc ggccaagggc aagctcgcag gcaccggcgt cgtcgtcgag    4500
acgatcaccg acgtactgga ccgcgggcgg tcactcgccg acgcaccgct ctacgtgccc    4560
gacgagaccg accgctgac ccttctcatc tacacctccg gcagcaccgg cactcccaag    4620
ggcgcgatgt accccgagtc caagaccgcc acgatgtggc aggccgggtc caaggcccgg    4680
tgggacgaga ccctcggcgt gatgccgtca atcaccctga acttcatgcc catgagtcac    4740
gtcatggggc gcggcatcct gtgcagcaca ctcgccagcg gcgaaccgc gtacttcgcc    4800 gcacgcagcg acctgtccac cttcctggag gacctcgccc tcgtgcggcc cacgcagctc    4860
aacttcgttc ctcgcatctg ggacatgctg ttccaggagt accagagccg cctcgacaac    4920
cgccgcgccg agggatccga ggaccgagcc gaagccgcag tcctcgaaga ggtccgcacc    4980
caactgctcg gcgggcgatt cgtttcggcc ctgaccggat cggctcccat ctcggcgag    5040 atgaagagct gggtcgagga cctgctcgac atgcatctgc tggagggcta cggctccacc    5100
gaggccggcc cggtgttcat cgacgggcag atccagcgcc cgccggtcat cgactacaag    5160
ctggtcgacg tgcccgatct cggctacttc gccacggacc ggccctaccc gcgcggcgaa    5220
cttctggtca gtccgagca gatgttcccc ggctactaca agcgtccgga gatcaccgcc    5280
gagatgttcg acgaggacgg gtactaccgc accggcgaca tcgtcgccga gctcgggccc    5340
gaccatctcg aatacctcga ccgccgcaac aacgtgctga aactgtcgca gggcgaattc    5400
gtcacggtct ccaagctgga ggcggtgttc ggcgacagcc ccctggtacg ccagatctac    5460
gtctacggca acagcgcgcg gtcctatctg ctggcggtcg tggtcccgac cgaagaggca    5520
```

```
ctgtcacgtt gggacggtga cgaactcaag tcgcgcatca gcgactcact gcaggacgcg    5580
gcacgagccg ccggattgca gtcgtatgag atcccgcgtg acttcctcgt cgagacaaca    5640
cctttcacgc tggagaacgg cctgctgacc ggtatccgca agctggcccg ccgaaactg     5700
aaggcgcact acgcgaacg cctcgaacag ctctacaccg acctggccga ggggcaggcc     5760
aacgagttgc gcgagttgcg ccgcaacgga gccgaccggc ccgtggtcga gaccgtcagc    5820
cgcgccgcgg tcgcactgct cggtgcctcc gtcacggatc tgcggtccga tgcgcacttc    5880
accgatctgg gtggagattc gttgtcggcc ttgagcttct cgaacctgtt gcacgagatc    5940
ttcgatgtcg acgtgccggt cggcgtcatc gtcagcccgg ccaccgacct ggcaggcgtc    6000
gcggcctaca tcgagggcga actgcgcggc tccaagcgcc ccacatacgc gtcggtgcac    6060
gggcgcgacg ccaccgaggt gcgcgcgcgt gatctcgccc tgggcaagtt catcgacgcc    6120
aagaccctgt ccgccgcgcc gggtctgccg cgttcgggca ccgagatccg caccgtgctg    6180
ctgaccggcg ccaccgggtt cctgggccgc tatctggcgc tggaatggct ggagcgcatg    6240
gacctggtgg acggcaaggt gatctgcctg gtgcgcgccc gcagcgacga cgaggcccgg    6300
gcgcgtctgg acgccacgtt cgacaccggg gacgcgacac tgctcgagca ctaccgcgcg    6360
ctggcagccg atcacctcga ggtgatcgcc ggtgacaagg gcgaggccga tctgggtctc    6420
gaccacgaca cgtggcagcg actggccgac accgtcgatc tgatcgtcga tccggccgcc    6480
ctggtcaatc acgtcctgcc gtacagccag atgttcggac ccaatgcgct cggcaccgcc    6540
gaactcatcc ggatcgcgct gaccaccacg atcaagccgt acgtgtacgt ctcgacgatc    6600
ggtgtgggac agggcatctc ccccgaggcg ttcgtcgagg acgccgacat ccgcgagatc    6660
agcgcgacgc gccgggtcga cgactcgtac gccaacggct acggcaacag caagtgggcc    6720
ggcgaggtcc tgctgcggga ggcgcacgac tggtgtggtc tgccggtctc ggtgttccgc    6780
tgcgacatga tcctggccga cacgacctac tcgggtcagc tgaacctgcc ggacatgttc    6840
acccgcctga tgctgagcct cgtggcgacc ggcatcgcgc ccggttcgtt ctacgaactc    6900
gatgcggacg gcaaccggca gcgcgcccac tacgacgggc tgcccgtgga gttcatcgcc    6960
gaggcgatct ccaccatcgg ctcgcaggtc accgacggat tcgagacgtt ccacgtgatg    7020
aacccgtacg acgacggcat cggcctcgac gagtacgtgg actggctgat cgaggccggc    7080
taccccgtgc accgcgtcga cgactacgcc acctggctga ccggttcga aaccgcactg      7140
cgggccctgc cggaacggca acgtcaggcc tcgctgctgc cgctgctgca caactatcag    7200
cagccctcac cgcccgtgtg cggtgccatg gcacccaccg accggttccg tgccgcggtg    7260
caggacgcga agatcggccc cgacaaggac attccgcacg tcacggccga cgtgatcgtc    7320
aagtacatca gcaacctgca gatgctcgga ttgctgtaag agaaggagtt ctatcatgat    7380
cgagacaatt ttgcctgctg gtgtcgagtc ggctgagctg ctggagtatc cggaggacct    7440
gaaggcgcat ccggcggagg agcatctcat cgcgaagtcg gtggagaagc ggcgccggga    7500
cttcatcggg gccaggcatt gtgcccggct ggcgctggct gagctcggcg agccgccggt    7560
ggcgatcggc aaaggggagc ggggtgcgcc gatctggccg cgcggcgtcg tcggcagcct    7620
cacccattgc gacggatatc gggcgcggc ggtggcgcac aagatgcgct tccgttcgat     7680
cggcatcgat gccgagccgc acgcgacgct gcccgaaggc gtgctggatt cggtcagcct    7740
gccgccggag cgggagtggt tgaagaccac cgattccgca ctgcacctgg accgtttact    7800
gttctgcgca aaggaagcca cctacaaggc gtggtggccg ctgaccgcgc gctggctcgg    7860
cttcgaggaa gcgcacatca ccttcgagat cgaagacggc tccgccgatt ccggcaacgg    7920
```

| | |
|---|---|
| cacctttcac agcgagctgc tggtgccggg acagacgaat gacggtggga cgccgctgct | 7980 |
| ttcgttcgac ggccggtggc tgatcgccga cgggttcatc ctcaccgcga tcgcgtacgc | 8040 |
| ctgataa | 8047 |

<210> SEQ ID NO 11
<211> LENGTH: 1137
<212> TYPE: DNA
<213> ORGANISM: Bacillus subtilis

<400> SEQUENCE: 11

| | |
|---|---|
| atgatcatag gggttcctaa agagataaaa aacaatgaaa accgtgtcgc attaacaccc | 60 |
| gggggcgttt ctcagctcat ttcaaacggc caccgggtgc tggttgaaac aggcgcgggc | 120 |
| cttggaagcg gatttgaaaa tgaagcctat gagtcagcag gagcggaaat cattgctgat | 180 |
| ccgaagcagg tctgggacgc cgaaatggtc atgaaagtaa agaaccgct gccggaagaa | 240 |
| tatgtttatt ttcgcaaagg acttgtgctg tttacgtacc ttcatttagc agctgagcct | 300 |
| gagcttgcac aggccttgaa ggataaagga gtaactgcca tcgcatatga aacggtcagt | 360 |
| gaaggccgga cattgcctct tctgacgcca atgtcagagg ttgcgggcag aatggcagcg | 420 |
| caaatcggcg ctcaattctt agaaaagcct aaaggcggaa aaggcattct gcttgccggg | 480 |
| gtgcctggcg tttcccgcgg aaaagtaaca attatcggag gaggcgttgt cgggacaaac | 540 |
| gcggcgaaaa tggctgtcgg cctcggtgca gatgtgacga tcattgactt aaacgcagac | 600 |
| cgcttgcgcc agcttgatga catcttcggc catcagatta aaacgttaat ttctaatccg | 660 |
| gtcaatattg ctgatgctgt ggcggaagcg gatctcctca tttgcgcggt attaattccg | 720 |
| ggtgctaaag ctccgactct tgtcactgag gaaatggtaa acaaatgaa acccggttca | 780 |
| gttattgttg atgtagcgat cgaccaaggc ggcatcgtcg aaactgtcga ccatatcaca | 840 |
| acacatgatc agccaacata tgaaaaacac ggggttgtgc attatgctgt agcgaacatg | 900 |
| ccaggcgcag tccctcgtac atcaacaatc gccctgacta acgttactgt tccatacgcg | 960 |
| ctgcaaatcg cgaacaaagg ggcagtaaaa gcgctcgcag acaatacggc actgagagcg | 1020 |
| ggtttaaaca ccgcaaacgg acacgtgacc tatgaagctg tagcaagaga tctaggctat | 1080 |
| gagtatgttc ctgccgagaa agctttacag gatgaatcat ctgtggcggg tgcttaa | 1137 |

<210> SEQ ID NO 12
<211> LENGTH: 1380
<212> TYPE: DNA
<213> ORGANISM: Chromobacterium violaceum

<400> SEQUENCE: 12

| | |
|---|---|
| atgcagaaac agcgtaccac ctctcagtgg cgtgaactcg atgcggcgca tcatctccat | 60 |
| ccgtttaccg ataccgcgag cctcaatcag gcgggtgcgc gtgtgatgac ccgtggcgaa | 120 |
| ggcgtgtatc tctgggatag cgaaggcaac aaaattattg atggcatggc gggcctctgg | 180 |
| tgcgtgaacg tgggctatgg ccgtaaagat tttgcggaag cggcgcgtcg tcagatggaa | 240 |
| gaactcccgt tttataacac cttctttaaa accaccatcc cggcggtggt ggaactcagc | 300 |
| agcctcctcg ccgaagttac cccggcaggt tttgatcgtg tgttttatac caacagcggc | 360 |
| agcgaaagcg tggataccat gattcgtatg gtgcgtcgtt attgggatgt gcagggcaaa | 420 |
| ccggaaaaaa aaccctcat tggccgttgg aacggctatc acggcagcac cattggcggt | 480 |
| gcgagcctcg gcggcatgaa atatatgcat gaacagggcg atctcccgat tccgggcatg | 540 |

```
gcgcatattg aacagccgtg gtggtataaa catggcaaag atatgacccc ggatgaattt      600
ggcgtggttg cggcgcgttg gctcgaagaa aaaattctcg aaatcggcgc ggataaagtg      660
gcggcgtttg tgggcgaacc gattcagggt gcgggcggtg tgattgttcc gccggcaacc      720
tattggccgg aaattgaacg tatttgccgc aaatatgatg tgctcctcgt tgcggatgaa      780
gtgatttgcg gctttggccg taccggcgaa tggtttggcc atcagcattt tggctttcag      840
ccggacctct ttaccgcggc gaaaggcctc agcagcggct atctcccgat tggcgcggtg      900
tttgtgggca acgtgttgc ggaaggtctc attgcgggcg gtgattttaa ccatggcttt      960
acctatagcg gccatccggt gtgtgcggcg gtggcgcatg cgaatgttgc ggcgctccgt     1020
gatgaaggca ttgtgcagcg tgtgaaagat gatattggcc cgtatatgca gaaacgttgg     1080
cgtgaaacct ttagccgttt tgaacatgtg gatgatgtgc gtggcgtggg catggtgcag     1140
gcgtttaccc tcgtgaaaaa caaagcgaaa cgtgaactct ttccggattt tggcgaaatt     1200 ggcacctct gccgcgatat tttttttcgc aacaacctca ttatgcgtgc gtgcggcgat     1260
cacattgtgt ctgcaccgcc gctcgttatg acccgtgcgg aagtggatga atgctcgcc     1320 gtggcggaac gttgcctcga gaatttgaa cagaccctca aagcgcgtgg cctcgcctaa     1380

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
atgatcatag gggttcctaa agag                                              24

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ttaagcaccc gccacagatg                                                   20

<210> SEQ ID NO 15
<211> LENGTH: 6866
<212> TYPE: DNA
<213> ORGANISM: Artificial Sequence
<220> FEATURE:
<223> OTHER INFORMATION: Vector

<400> SEQUENCE: 15
atgatcatag gggttcctaa agagataaaa aacaatgaaa accgtgtcgc attaacaccc       60
gggggcgttt ctcagctcat ttcaaacggc caccgggtgc tggttgaaac aggcgcgggc      120
cttggaagcg gatttgaaaa tgaagccatt gagtcagcag gagcggaaat cattgctgat      180
ccgaagcagg tctgggacgc cgaaatggtc atgaaagtaa agaaccgct gccggaagaa      240 tatgtttatt tcgcaaagg acttgtgctg tttacgtacc ttcatttagc agctgagcct      300
gagcttgcac aggccttgaa ggataaagga gtaactgcca tcgcatatga acggtcagt      360 gaaggccgga cattgcctct tctgacgcca atgtcagagg ttgcgggcag aatggcagcg      420
caaatcggcg ctcaattctt agaaaagcct aaggcggaa aaggcattct gcttgccggg      480
gtgcctggcg tttccgcgg aaaagtaaca attatcggag gaggcgttgt cgggacaaac      540
```

```
gcggcgaaaa tggctgtcgg cctcggtgca gatgtgacga tcattgactt aaacgcagac    600
cgcttgcgcc agcttgatga catcttcggc catcagatta aaacgttaat ttctaatccg    660
gtcaatattg ctgatgctgt ggcggaagcg gatctcctca tttgcgcggt attaattccg    720
ggtgctaaag ctccgactct tgtcactgag gaaatggtaa aacaaatgaa acccggttca    780
gttattgttg atgtagcgat cgaccaaggc ggcatcgtcg aaactgtcga ccatatcaca    840
acacatgatc agccaacata tgaaaaacac ggggttgtgc attatgctgt agcgaacatg    900
ccaggcgcag tccctcgtac atcaacaatc gccctgacta acgttactgt tccatacgcg    960
ctgcaaatcg cgaacaaagg ggcagtaaaa gcgctcgcag acaatacggc actgagagcg   1020
ggtttaaaca ccgcaaacgg acacgtgacc tatgaagctg tagcaagaga tctaggctat   1080
gagtatgttc ctgccgagaa agctttacag gatgaatcat ctgtggcggg tgcttaatta   1140
aggagatata atatgcagaa acagcgtacc acctctcagt ggcgtgaact cgatgcggcg   1200
catcatctcc atccgtttac cgataccgcg agcctcaatc aggcgggtgc gcgtgtgatg   1260
acccgtggcg aaggcgtgta tctctgggat agcgaaggca caaaattat tgatggcatg   1320 gcgggcctct ggtgcgtgaa cgtgggctat ggccgtaaag attttgcgga agcggcgcgt   1380
cgtcagatgg aagaactccc gttttataac accttcttta aaaccaccca tccggcggtg   1440
gtggaactca gcagcctcct cgccgaagtt accccggcag gttttgatcg tgtgttttat   1500
accaacagcg gcagcgaaag cgtggatacc atgattcgta tggtgcgtcg ttattgggat   1560
gtgcagggca aaccggaaaa aaaaaccctc attggccgtt ggaacggcta tcacggcagc   1620
accattggcg gtgcgagcct cggcggcatg aaatatatgc atgaacaggg cgatctcccg   1680
attccgggca tggcgcatat tgaacagccg tggtggtata acatggcaa agatatgacc   1740 ccggatgaat ttggcgtggt tgcggcgcgt tggctcgaag aaaaaattct cgaaatcggc   1800
gcggataaag tggcggcgtt tgtgggcgaa ccgattcagg gtgcgggcgg tgtgattgtt   1860
ccgccggcaa cctattggcc ggaaattgaa cgtatttgcc gcaaatatga tgtgctcctc   1920
gttgcggatg aagtgatttg cggctttggc cgtaccggcg aatggtttgg ccatcagcat   1980
tttggctttc agccggacct cttttaccgcg gcgaaaggcc tcagcagcgg ctatctcccg   2040
attggcgcgg tgtttgtggg caaacgtgtt gcggaaggtc tcattgcggg cggtgatttt   2100
aaccatggct ttacctatag cggccatccg gtgtgtgcgg cggtggcgca tgcgaatgtt   2160
gcggcgctcc gtgatgaagg cattgtgcag cgtgtgaaag atgatattgg cccgtatatg   2220
cagaaacgtt ggcgtgaaac cttagccgt tttgaacatg tggatgatgt gcgtggcgtg   2280
ggcatggtgc aggcgtttac cctcgtgaaa aacaaagcga aacgtgaact ctttccggat   2340
tttggcgaaa ttggcaccct ctgccgcgat atttttttc gcaacaacct cattatgcgt   2400
gcgtgcggcg atcacattgt gtctgcaccg ccgctcgtta tgacccgtgc ggaagtggat   2460
gaaatgctcg ccgtggcgga acgttgcctc gaagaatttg aacagaccct caaagcgcgt   2520
ggcctcgcct aataatctag atcaacaact ctcctggcgc accatcgtcg gctacagcct   2580
cgggaattgc tgcaagtcga cggatcgccg gaattaattc tcatgtttga cagcttatca   2640
ctgatcagtg aattaatggc gatgacgcat cctcacgata atatccgggt aggcgcaatc   2700
actttcgtct ctactccgtt acaaagcgag gctgggtatt tcccggcctt tttgggccgg   2760
ccggatcccc ccacttcaga agttcctata cactagagaa taggaacttc actatagagt   2820
cgaataaggg cgacaccccc taattagccc gggcgaaagg cccagtcttt cgactgagcc   2880
```

```
tttcgtttta tttgatgcct ggcagttccc tactctcgca tggggagtcc ccacactacc    2940
atcggcgcta cggcgtttca cttctgagtt cggcatgggg tcaggtggga ccaccgcgct    3000
actgccgcca ggcaaacaag gggtgttatg agccatattc aggtataaat gggctcgcga    3060
taatgttcag aattggttaa ttggttgtaa cactgacccc tatttgttta tttttctaaa    3120
tacattcaaa tatgtatccg ctcatgagac aataaccctg ataaatgctt caataatatt    3180
gaaaaaggaa gaatatgagc catattcaac gggaaacgtc gaggccgcga ttaaattcca    3240
acatggatgc tgatttatat gggtataaat gggctcgcga taatgtcggg caatcaggtg    3300
cgacaatcta tcgcttgtat gggaagcccg atgcgccaga gttgtttctg aaacatggca    3360
aaggtagcgt tgccaatgat gttacagatg agatggtcag actaaactgg ctgacggaat    3420
ttatgccact tccgaccatc aagcatttta tccgtactcc tgatgatgca tggttactca    3480
ccactgcgat ccccggaaaa acagcgttcc aggtattaga agaatatcct gattcaggtg    3540
aaaatattgt tgatgcgctg gcagtgttcc tgcgccggtt gcactcgatt cctgtttgta    3600
attgtccttt taacagcgat cgcgtatttc gcctcgctca ggcgcaatca cgaatgaata    3660
acggtttggt tgatgcgagt gattttgatg acgagcgtaa tggctggcct gttgaacaag    3720
tctggaaaga aatgcataaa cttttgccat tctcaccgga ttcagtcgtc actcatggtg    3780
atttctcact tgataacctt attttttgacg aggggaaatt aataggttgt attgatgttg    3840
gacgagtcgg aatcgcagac cgataccagg atcttgccat cctatggaac tgcctcggtg    3900
agttttctcc ttcattacag aaacggcttt tcaaaaata tggtattgat aatcctgata    3960
tgaataaatt gcagtttcat ttgatgctcg atgagttttt ctaaaagcgg cgcgccatcg    4020
aatggcgcaa aacctttcgc ggtatggcat gatagcgccc ggaagagagt caattcaggg    4080
tggtgaatat gaaaccagta acgttatacg atgtcgcaga gtatgccggt gtctcttatc    4140
agaccgtttc ccgcgtggtg aaccaggcca gccacgtttc tgcgaaaacg cgggaaaaag    4200
tggaagcggc gatggcggag ctgaattaca ttcccaaccg cgtggcacaa caactggcgg    4260
gcaaacagtc gttgctgatt ggcgttgcca cctccagtct ggccctgcac gcgccgtcgc    4320
aaattgtcgc ggcgattaaa tctcgcgccg atcaactggg tgccagcgtg gtggtgtcga    4380
tggtagaacg aagcggcgtc gaagcctgta aagcggcggt gcacaatctt ctcgcgcaac    4440
gcgtcagtgg gctgatcatt aactatccgc tggatgacca ggatgccatt gctgtggaag    4500
ctgcctgcac taatgttccg gcgttatttc ttgatgtctc tgaccagaca cccatcaaca    4560
gtattatttt ctcccatgag gacggtacgc gactgggcgt ggagcatctg gtcgcattgg    4620
gtcaccagca aatcgcgctg ttagcgggcc cattaagttc tgtctcggcg cgtctgcgtc    4680
tggctggctg gcataaatat ctcactcgca atcaaattca gccgatagcg gaacgggaag    4740
gcgactggag tgccatgtcc ggttttcaac aaaccatgca aatgctgaat gagggcatcg    4800
ttcccactgc gatgctggtt gccaacgatc agatggcgct gggcgcaatg cgcgccatta    4860
ccgagtccgg gctgcgcgtt ggtgcggata tctcggtagt gggatacgac gataccgaag    4920
atagctcatg ttatatcccg ccgttaacca ccatcaaaca ggattttcgc ctgctggggc    4980
aaaccagcgt ggaccgcttg ctgcaactct ctcagggcca ggcggtgaag ggcaatcagc    5040
tgttgccagt ctcactggtg aaaagaaaaa ccaccctggc gcccaatacg caaaccgcct    5100
ctccccgcgc gttggccgat tcattaatgc agctggcacg acaggtttcc cgactggaaa    5160
gcgggcagtg actcatgacc aaaatccctt aacgtgagtt acgcgcgcgt cgttccactg    5220
agcgtcagac cccgtagaaa agatcaaagg atcttcttga gatcctttt ttctgcgcgt    5280
```

```
aatctgctgc ttgcaaacaa aaaaaccacc gctaccagcg gtggtttgtt tgccggatca    5340
agagctacca actcttttc cgaaggtaac tggcttcagc agagcgcaga taccaaatac    5400
tgttcttcta gtgtagccgt agttagccca ccacttcaag aactctgtag caccgcctac    5460
atacctcgct ctgctaatcc tgttaccagt ggctgctgcc agtggcgata agtcgtgtct    5520 taccggggttg gactcaagac gatagttacc ggataaggcg cagcggtcgg gctgaacggg    5580
gggttcgtgc acacagccca gcttggagcg aacgacctac accgaactga gatacctaca    5640
gcgtgagcta tgagaaagcg ccacgcttcc cgaagggaga aggcggaca  ggtatccggt    5700 aagcggcagg gtcggaacag gagagcgcac gagggagctt ccaggggaa  acgcctggta    5760 tctttatagt cctgtcgggt ttcgccacct ctgacttgag cgtcgatttt tgtgatgctc    5820
gtcagggggg cggagcctat ggaaaaacgc cagcaacgcg gcctttttac ggttcctggc    5880
cttttgctgg ccttttgctc acatgttctt tcctgcgtta tccctgatt ctgtggataa    5940 ccgtattacc gcctttgagt gagctgatac cgctcgccgc agccgaacga ccgagcgcag    6000
cgagtcagtg agcgaggaag cggaaggcga gagtagggaa ctgccaggca tcaaactaag    6060
cagaaggccc ctgacggatg ccttttttgc gtttctacaa actctttctg tgttgtaaaa    6120
cgacggccag tcttaagctc gggcccctg  gcgggttctg ataacgagta atcgttaatc    6180
cgcaaataac gtaaaaaccc gcttcggcgg gtttttttat gggggggagtt tagggaaaga    6240 gcatttgtca gaatatttaa gggcgcctgt cactttgctt gatatatgag aattatttaa    6300
ccttataaat gagaaaaaag caacgcactt taaataagat acgttgcttt ttcgattgat    6360
gaacacctat aattaaacta ttcatctatt atttatgatt ttttgtatat acaatatttc    6420
tagtttgtta aagagaatta agaaaataaa tctcgaaaat aataagggaa aaatcagttt    6480
ttgatatcaa aattatacat gtcaacgata atacaaaata taatacaaac tataagatgt    6540
tatcagtatt tattatgcat ttagaataaa ttttgtgtcg cccttattcg actcactata    6600
gaagttccta ttctctagta agtataggaa cttcacttca ttttggatcc ggccggcctg    6660 cagcccgca  gggcctgtct cggtcgatca ttcagcccgg ctcatagata tgcgggcagt    6720
gagcgcaacg caattaatgt aagttagctc actcattagg cacccagcc  ttgacactt     6780 atgcttccgg ctcgtataat gtgtggaatt gtgagcggat aacaataaca attcacaca    6840 ggatctagga accaaggaga gtggca                                         6866
```

<210> SEQ ID NO 16
<211> LENGTH: 1857
<212> TYPE: DNA
<213> ORGANISM: Oryza sativa

<400> SEQUENCE: 16

```
atgggttctg gtctgttcaa gccgcgtgtt caccccggatc tgcgtgacgt tttctctaaa      60
atgtctttct tcgacaaaat cggtttcctg ttcatccacg cgttcgacaa acgtaacctg     120
tggcacaaag ttccggttcc gatcggtctg ctgtacctga acacccgtcg tacctgctg     180 gaaaaataca atctgctggc cgttggtcgt tcttctcacg gtgcgctgtt cgacccaaaa     240
gaattcctgt accgtaccga agatggtaaa tacaatgacc cgcacaacgc ggaagccggc     300
tctcaaaaca ccttctttgg tcgcaacatg gagccggttg accagcagga cgaactgatg     360
tctccggacc cgttcgttgt tgcgaccaaa ctgctggcgc gtcgtgaata caaagacacc     420
ggcaaacagt tcaacatcct ggcggcagcg tggatccagt tcatggttca cgattggatg     480
```

```
gaccacatgg aggacaccgg tcaaattggt atcaccgcgc cgaaagaagt tgcgaacgaa      540
tgcccgctga atctttcaa attccacccg acgaaagaac tgccgaccaa ctctgacggt       600
atcaaaatcg gtcactacaa catccgtacc gcgtggtggg acggttctgc ggtttacggt      660
aacaatgaag aacgtgcgga aaaactgcgt acctacgttg acggtaaaact ggttatcggt     720 gatgacggtc tgctgctgca caaagaaaac ggtgttgcgc tgtctggtga catccgcaac     780
tcttgggcgg cgttttctat cctgcaggct ctgttcgtta agaacacaa cgcggtttgc      840 gacgcgatca aggaagaaca cccgaacctg tctgacgaag aactgtaccg ttacgcgaaa     900
ctggttacct ctgcggttat cgcgaaagtt cacaccatcg actggaccgt tgaactgctg    960
aagaccaaaa ccatgcgtgc ggcgatgcgt gcgaactggt acggcctgct gggtaaaaaa     1020
atcaaagaca cctttggcca catcggtggt ccgatcctgg tggtctggt tggtctgaaa      1080 aaaccaaaca accacggtgt tccgtactct ctgactgaag aattcacctc tgtgtatcgt     1140
atgcactctc tgatcccgtc taccctgaaa ctgcgtgacc cgaccggtca gccggacgcg     1200
aataactctc cgccgtgcct ggaagacatc gacatcggtg agatgatcgg tctgaaaggt     1260
gaggaacagc tgtctaaaat tggcttcgaa aaacaggcgc tgtctatggg ttaccaggcg    1320
tgtggtgcgc tggaactgtg gaactacccg tcttcttcc gtaacctgat cccacagaac      1380
ctggacggta ccaatcgttc tgaccgtatc gacctggcgg cgctggaagt ttatcgtgac     1440
cgtgaacgtt ctgttccgcg ttacaacgaa ttccgtcgtc gtctgttcct gatcccgatc     1500
aaatcttggg aagacctgac ctctgacaaa gacgcgattg aaaccatccg tgcgatctac     1560
ggtgacgacg ttgaaaaaaact ggacctgctg gttggtctga tggcggaaaaa gaaaatcaaa    1620 ggcttcgcga tctctgaaac cgcgttcaac atcttcatcc tgatggcttc tcgtcgtctg     1680
gaagcggacc gtttcttcac ctccaacttc aacgaagaga cgtacaccaa aaaaggtatg    1740
cagtgggtta aaaccaccga aggtctgcgc gacgttatca accgtcacta tccggaaatc     1800
accgcgaaat ggatgaaatc ttcttctgcg ttctctgttt gggacgcgga ctactag        1857
```

<210> SEQ ID NO 17
<211> LENGTH: 5704
<212> TYPE: DNA
<213> ORGANISM: Artificial Sequence
<220> FEATURE:
<223> OTHER INFORMATION: vector

<400> SEQUENCE: 17

```
ctaggctgct gccaccgctg agcaataact agcataaccc cttggggcct ctaaacgggt      60 cttgagggt ttttgctga aacctcaggc atttgagaag cacacggtca cactgcttcc       120
ggtagtcaat aaaccggtaa accagcaata gacataagcg gctatttaac gaccctgccc     180
tgaaccgacg accgggtcga atttgctttc gaatttctgc cattcatccg cttattatca     240
cttattcagg cgtagcacca ggcgtttaag ggcaccaata actgccttaa aaaaattacg     300
ccccgccctg ccactcatcg cagtactgtt gtaattcatt aagcattctg ccgacatgga     360
agccatcaca gacggcatga tgaacctgaa tcgccagcgg catcagcacc ttgtcgcctt     420
gcgtataata tttgcccata gtgaaaacgg gggcgaagaa gttgtccata ttggccacgt     480
ttaaatcaaa actggtgaaa ctcacccagg gattggctga cgaaaaac atattctcaa      540 taaacccttt agggaaatag gccaggtttt caccgtaaca cgccacatct tgcgaatata    600
tgtgtagaaa ctgccggaaa tcgtcgtggt attcactcca gagcgatgaa acgtttcag    660 tttgctcatg gaaaacggtg taacaagggt gaacactatc ccatatcacc agctcaccgt     720
```

```
ctttcattgc catacggaac tccggatgag cattcatcag gcgggcaaga atgtgaataa      780
aggccggata aaacttgtgc ttattttct ttacggtctt taaaaaggcc gtaatatcca      840
gctgaacggt ctggttatag gtacattgag caactgactg aaatgcctca aaatgttctt      900
tacgatgcca ttgggatata tcaacggtgg tatatccagt gatttttttc tccatttttag     960 cttccttagc tcctgaaaat ctcgataact caaaaaatac gcccggtagt gatcttattt     1020
cattatggtg aaagttggaa cctcttacgt gccgatcaac gtctcatttt cgccaaaagt     1080
tggcccaggg cttcccggta tcaacaggga caccaggatt tatttattct gcgaagtgat     1140
cttccgtcac aggtatttat tcggcgcaaa gtgcgtcggg tgatgctgcc aacttactga     1200
tttagtgtat gatggtgttt ttgaggtgct ccagtggctt ctgtttctat cagctgtccc     1260
tcctgttcag ctactgacgg ggtggtgcgt aacggcaaaa gcaccgccgg acatcagcgc     1320
tagcggagtg tatactggct tactatgttg cactgatga gggtgtcagt gaagtgcttc      1380
atgtggcagg agaaaaaagg ctgcaccggt gcgtcagcag aatatgtgat acaggatata     1440
ttccgcttcc tcgctcactg actcgctacg ctcggtcgtt cgactgcggc gagcggaaat     1500
ggcttacgaa cggggcggag atttcctgga agatgccagg aagatactta acagggaagt     1560
gagagggccg cggcaaagcc gttttccat aggctccgcc cccctgacaa gcatcacgaa      1620
atctgacgct caaatcagtg gtggcgaaac ccgacaggac tataaagata ccaggcgttt     1680 ccccctggcgg ctccctcgtg cgctctcctg ttcctgcctt tcggtttacc ggtgtcattc    1740
cgctgttatg gccgcgtttg tctcattcca gccctgacac tcagttccgg gtaggcagtt     1800
cgctccaagc tggactgtat gcacgaaccc ccgttcagt ccgaccgctg cgccttatcc      1860
ggtaactatc gtcttgagtc caacccggaa agacatgcaa aagcaccact ggcagcagcc     1920
actggtaatt gatttagagg agttagtctt gaagtcatgc gccggttaag gctaaactga     1980
aaggacaagt tttggtgact gcgctcctcc aagccagtta cctcggttca aagagttggt     2040
agctcagaga accttcgaaa aaccgccctg caaggcggtt ttttcgtttt cagagcaaga     2100
gattacgcgc agaccaaaac gatctcaaga agatcatctt attaatcaga taaaatattt     2160
ctagatttca gtgcaattta tctcttcaaa tgtagcacct gaagtcagcc ccatacgata     2220
taagttgtaa ttctcatgtt agtcatgccc cgcgcccacc ggaaggagct gactgggttg     2280
aaggctctca agggcatcgg tcgagatccc ggtgcctaat gagtgagcta acttacatta     2340
attgcgttgc gctcactgcc cgctttccag tcgggaaacc tgtcgtgcca gctgcattaa     2400
tgaatcggcc aacgcgcggg gagaggcggt ttgcgtattg ggcgccaggg tggttttct      2460 tttcaccagt gagacgggca acagctgatt gcccttcacc gcctggccct gagagagttg     2520
cagcaagcgg tccacgctgg tttgccccag caggcgaaaa tcctgtttga tggtggttaa     2580
cggcgggata taacatgagc tgtcttcggt atcgtcgtat cccactaccg agatgtccgc     2640
accaacgcgc agcccggact cggtaatggc gcgcattgcg cccagcgcca tctgatcgtt     2700
ggcaaccagc atcgcagtgg gaacgatgcc ctcattcagc atttgcatgg tttgttgaaa     2760
accggacatg gcactccagt cgccttcccg ttccgctatc ggctgaattt gattgcgagt     2820
gagatattta tgccagccag ccagacgcag acgcgccgga acagaactta atgggcccgc     2880
taacagcgcg atttgctggt gacccaatgc gaccagatgc tccacgccca gtcgcgtacc     2940
gtcttcatgg gagaaaataa tactgttgat gggtgtctgg tcagagacat caagaaataa     3000
cgccggaaca ttagtgcagg cagcttccac agcaatggca tcctggtcat ccagcggata     3060
```

```
gttaatgatc agcccactga cgcgttgcgc gagaagattg tgcaccgccg ctttacaggc    3120
ttcgacgccg cttcgttcta ccatcgacac caccacgctg gcacccagtt gatcggcgcg    3180
agatttaatc gccgcgacaa tttgcgacgg cgcgtgcagg gccagactgg aggtggcaac    3240
gccaatcagc aacgactgtt tgcccgccag ttgttgtgcc acgcggttgg gaatgtaatt    3300
cagctccgcc atcgccgctt ccactttttc ccgcgttttc gcagaaacgt ggctggcctg    3360
gttcaccacg cgggaaacgg tctgataaga gacaccggca tactctgcga catcgtataa    3420
cgttactggt ttcacattca ccaccctgaa ttgactctct tccgggcgct atcatgccat    3480
accgcgaaag gttttgcgcc attcgatggt gtccggatcc tcgacgctct cccttatgcg    3540
actcctgctg gctatggtgg gatttccctt gctgaaatgg gagatccgat catgttcgag    3600
ctcttattca aatacactgc tgtgttggcg gtaagcgttc tcgagcgcgg ccgcgcgatc    3660
gcacctggtg tttaaacggc cggcccctgc aggggcagtg agcgcaacgc aattaatgta    3720
agttagctca ctcattaggc accccaggct tgacacttta tgcttccggc tcgtataatg    3780
tgtggaattg tgagcggata caataacaa tttcacacag gatctaggaa ccaaggagag    3840
tggcatatgg gttctggtct gttcaagccg cgtgttcacc cggatctgcg tgacgttttc    3900
tctaaaatgt ctttcttcga caaatcggtt ttcctgttca tccacgcgtt cgacaaacgt    3960
aacctgtggc acaaagttcc ggttccgatc ggtctgctgt acctgaacac ccgtcgtacc    4020
ctgctggaaa atacaatct gctggccgtt ggtcgttctt ctcacggtgc gctgttcgac    4080
ccaaaagaat tcctgtaccg taccgaagat ggtaaataca atgacccgca caacgcggaa    4140
gccggctctc aaaacacctt ctttggtcgc aacatggagc cggttgacca gcaggacgaa    4200
ctgatgtctc cggacccgtt cgttgttgcg accaaactgc tggcgcgtcg tgaatacaaa    4260
gacaccggca aacagttcaa catcctggcg gcagcgtgga tccagttcat ggttcacgat    4320
tggatggacc acatggagga caccggtcaa attggtatca ccgcgccgaa agaagttgcg    4380
aacgaatgcc cgctgaaatc tttcaaattc caccccgacga aagaactgcc gaccaactct    4440
gacggtatca aaatcggtca ctacaacatc cgtaccgcgt ggtgggacgg ttctgcggtt    4500
tacggtaaca atgaagaacg tgcggaaaaa ctgcgtacct acgttgacgg taaactggtt    4560
atcggtgatg acggtctgct gctgcacaaa gaaaacggtg ttgcgctgtc tggtgacatc    4620
cgcaactctt gggcgggcgt ttctatcctg caggctctgt tcgttaaaga acacaacgcg    4680
gtttgcgacg cgatcaagga agaacacccg aacctgtctg acgaagaact gtaccgttac    4740
gcgaaactgg ttacctctgc ggttatcgcg aaagttcaca ccatcgactg gaccgttgaa    4800
ctgctgaaga ccaaaaccat gcgtgcggcg atgcgtgcga actggtacgg cctgctgggt    4860
aaaaaaatca agacaccttt tggccacatc ggtggtccga tcctgggtgg tctggttggt    4920
ctgaaaaaac caaacaacca cggtgttccg tactctctga ctgaagaatt cacctctgtg    4980
tatcgtatgc actctctgat cccgtctacc ctgaaactgc gtgacccgac cggtcagccg    5040
gacgcgaata ctctccgcc gtgcctggaa gacatcgaca tcggtgagat gatcggtctg    5100
aaaggtgagg aacagctgtc taaaattggc ttcgaaaaac aggcgctgtc tatgggttac    5160
caggcgtgtg gtcgctgga actgtggaac tacccgtctt tcttccgtaa cctgatccca    5220
cagaacctgg acggtaccaa tcgttctgac cgtatcgacc tggcggcgct ggaagtttat    5280
cgtgaccgtg aacgttctgt tccgcgttac aacgaattcc gtcgtcgtct gttcctgatc    5340
ccgatcaaat cttgggaaga cctgaccctc gacaagacg cgattgaaac catccgtgcg    5400
atctacggtg acgacgttga aaaactggac ctgctggttg gtctgatggc ggaaaagaaa    5460
```

```
atcaaaggct tcgcgatctc tgaaaccgcg ttcaacatct tcatcctgat ggcttctcgt    5520
cgtctggaag cggaccgttt cttcacctcc aacttcaacg aagagacgta caccaaaaaa    5580
ggtatgcagt gggttaaaac caccgaaggt ctgcgcgacg ttatcaaccg tcactatccg    5640
gaaatcaccg cgaaatggat gaaatcttct tctgcgttct ctgtttggga cgcggactac    5700
tagc                                                                 5704
```